US011400165B2

(12) United States Patent
Krantz et al.

(10) Patent No.: US 11,400,165 B2
(45) Date of Patent: Aug. 2, 2022

(54) COMPOSITION AND METHOD FOR MODIFYING POLYPEPTIDES

(71) Applicant: Advanced Proteome Therapeutics Inc., Boston, MA (US)

(72) Inventors: Alexander Krantz, Boston, MA (US); Andrzej Wilczynski, lBoston, MA (US); Grzegorz Rymarczyk, Boston, MA (US)

(73) Assignee: ADVANCED PROTEOME THERAPEUTICS INC., Boston, MA (US)

( * ) Notice: Subject to any disclaimer, the term of this patent is extended or adjusted under 35 U.S.C. 154(b) by 386 days.

(21) Appl. No.: 16/180,960

(22) Filed: Nov. 5, 2018

(65) Prior Publication Data
US 2019/0175750 A1 Jun. 13, 2019

Related U.S. Application Data

(60) Provisional application No. 62/707,474, filed on Nov. 4, 2017, provisional application No. 62/764,086, filed on Jul. 18, 2018.

(51) Int. Cl.
*A61K 47/68* (2017.01)
*A61P 35/00* (2006.01)
*A61K 31/216* (2006.01)
*A61K 31/215* (2006.01)
*A61K 31/222* (2006.01)
*A61K 51/10* (2006.01)
*A61K 45/06* (2006.01)

(52) U.S. Cl.
CPC ........ *A61K 47/6889* (2017.08); *A61K 31/215* (2013.01); *A61K 31/216* (2013.01); *A61K 31/222* (2013.01); *A61P 35/00* (2018.01); *A61K 45/06* (2013.01); *A61K 51/10* (2013.01)

(58) Field of Classification Search
CPC .. A61K 47/6889; A61K 31/215; A61K 51/10; A61P 35/00
See application file for complete search history.

(56) References Cited

U.S. PATENT DOCUMENTS

| 4,833,092 | A | 5/1989 | Geysen |
| 5,010,175 | A | 4/1991 | Rutter et al. |
| 5,182,366 | A | 1/1993 | Huebner et al. |
| 5,270,170 | A | 12/1993 | Schatz et al. |
| 5,612,034 | A | 3/1997 | Pouletty et al. |
| 8,741,291 | B2 | 6/2014 | Bhat et al. |
| 2013/0052130 | A1 | 2/2013 | Davis et al. |
| 2016/0208021 | A1* | 7/2016 | Chang ................ C07K 16/2887 |
| 2017/0275331 | A1 | 9/2017 | Krantz et al. |

FOREIGN PATENT DOCUMENTS

| EP | 3222292 A1 * | 9/2017 | ............. A61P 35/02 |
| WO | 1992/000091 A1 | 1/1992 | |
| WO | 1992/009300 A1 | 6/1992 | |
| WO | 1993/006121 A1 | 4/1993 | |
| WO | 1993/020242 A1 | 10/1993 | |
| WO | 1994/006291 A1 | 3/1994 | |
| WO | 1994/006451 A1 | 3/1994 | |
| WO | 1995/028640 A1 | 10/1995 | |
| WO | 2007080114 A2 | 7/2007 | |
| WO | 2011/153250 A2 | 12/2011 | |
| WO | 2014/028803 A1 | 2/2014 | |
| WO | 2015/138907 A2 | 9/2015 | |

OTHER PUBLICATIONS

Dovgan et al., Acyl Fluorides: Fast, Efficient, and Versatile Lysine-Based Protein Conjugation via Plug-and-Play Strategy, Bioconjugate Chemistry, 28, 1452-1457, Publication Date: Apr. 26, 2017. (Year: 2017).*
Hapuarachchige et al., Bioorthogonal, two-component delivery systems based on antibody and drug-loaded nanocarriers for enhanced internalization of nanotherapeutics, Biomaterials, 35, 2346-2354, Publication Date: Dec. 15, 2013 (Year: 2013).*
ThermoScientific, User Guide: NHS-Azide and NHS-Phosphine Reagents (thermofisher.com), Publication Year: 2013 (Year: 2013).*
Pierce, Crosslinking Reagents, Technical Handbook, Publication Year: 2006 (Year: 2006).*
Anderl et al., Abstract 3616: Highly potent antibody-amanitin conjugates cause tumor-selective apoptosis, Proceedings: AACR 102nd Annual Meeting 2011—Apr. 2-6, 2011; Orlando, FL (Year: 2011).*
Thiele et al., An Eighteen-Membered Macrocyclic Ligand for Actinium-225 Targeted Alpha Therapy, Angew. Chem. Int. Ed. 2017, S6, 14712-14717, Publication Date: Oct. 16, 2017 (Year: 2017).*
Alves et al. (2012) "Small-molecule-based affinity chromatography method for antibody purification via nucleotide binding site targeting," Anal. Chem. 84:7721-8.
Alves et al. (Jun. 6, 2013) "Oriented antibody immobilization by site-specific UV photocrosslinking of biotin at the conserved nucleotide binding site for enhanced antigen detection," Biosens. Bioelectron. 49:387-393.
Anami et al. (2017) "Enzymatic Conjugation Using Branched Linkers for Constructing Homogeneous Antibody-Drug Conjugates with High Potency," The Royal Society of Chemistry, S1-S44.
Beck et al. (2010) "Strategies and challenges for the next generation of therapeutic antibodies," Nature Reviews, 10:345-352.
Berge et al. (1977) "Pharmaceutical salts," J. Pharm. Sci. 66:1-19.
Birtalan et al. (2008) "The intrinsic contributions of tyrosine, serine, glycine and arginine to the affinity and specificity of antibodies," J. Mol. Biol. 377(5):1518-1528.

(Continued)

*Primary Examiner* — Peter J Reddig
*Assistant Examiner* — Cheng Lu
(74) *Attorney, Agent, or Firm* — Lathrop GPM LLP; Brian C. Trinque

(57) ABSTRACT

The present disclosure provides methods for site-selectively crosslinking payloads to antibodies and other proteins. This can be accomplished using traceless affinity labels designed to label target proteins with bio-orthogonally reactive entities (ORE) using the compositions and methods described herein.

11 Claims, 11 Drawing Sheets

(56) References Cited

OTHER PUBLICATIONS

Delano et al. (2000) "Convergent solutions to binding at a protein-protein interface," Science. 287(5456):1279-83.
Dennler et al. (2013) "Enzymatic antibody modification by bacterial transglutaminase," Methods Mol. Biol. 2013;1045:205-15. doi: 10.1007/978-1-62703-541-5_12. Abstract only.
Dias et al. (2006) "Protein ligand design: from phage display to synthetic protein epitope mimetics in human antibody Fc-binding peptidomimetics," J. Am. Chem. Soc. 128:2726-2732.
Dommerholt et al. (2016) "Strain-Promoted 1,3-Dipolar Cycloaddition of Cycloalkynes and Organic Azides," Top Curr. Chem. (Z) 374 (16):1-20.
Fujishima et al. (2012) "Ligand-directed acyl imidazole chemistry for labeling of membrane-bound proteins on live cells," J. Am. Chem. Soc. 134(9):3961-3964.
Gordon et al. (1994) "Applications of combinatorial technologies to drug discovery. 2. Combinatorial organic synthesis, library screening strategies, and future directions," J. Med. Chem. 37(10):1387-401.
Handlogten et al. (2011) "Design of a heterobivalent ligand to inhibit IgE clustering on mast cells," Chem Biol. 18:1179-1188.
International Search Report with Written Opinion corresponding to International Patent Application No. PCT/US2017/016932, dated May 25, 2017.
Kolb et al. (2001) "Click Chemistry: Diverse Chemical Function from a Few Good Reactions," Angew. Chem. Int. Ed. 40:2004-2021.
Lac et al. (Dec. 17, 2015) "Covalent Chemical Ligation Strategy for Mono- and Polyclonal Immunoglobulins at Their Nucleotide Binding Sites," Bioconjugate Chem. 27(1):159-169.
Le Droumaguet et al. (2010) "Fluorogenic click reaction," Chem. Soc. Rev. 39(4):1233-1239.
London et al. (2010) "The structural basis of peptide-protein binding strategies," Structure. 18(2):188-199.
Pham et al. (2018) "Tuning a Protein-Labeling Reaction to Achieve Highly Site Selective Lysine Conjugation," ChemBioChem, 19:799-804.
Pubchem, Substance Record for SID 129533161. Available Date: Dec. 4, 2011. [retrieved on Dec. 31, 2018]. Retrieved from the Internet: <https://pubchem.ncbi.nlm.nih.gov/substance/129533161>.
Pubchem, Substance Record for SID 15735569. Available Date: Oct. 25, 2006. [retrieved on Dec. 31, 2018], Retrieved from the Internet: <https://pubchem.ncbi.nlm.nih.gov/substance/15735569>.
Rajagopalan et al. (1996) "Novel unconventional binding site in the variable region of immunoglobulins," Proc. Natl. Scad. Sci. USA. 93(12):6019-6024.
Thiele et al. (2017) "An Eighteen-Membered Macrocyclic Ligand for Actinium-225 Targeted Alpha Therapy," Angew. Chem. Int. Ed. 10.1002/anie.201709532.
Santos, Fabio M. F. et al., Modular Assembly of Reversible Multivalent Cancer-Cell-Targeting Drug Conjugates, Angew. Chem. Int. Ed., 2017, 56, 9346-9350.
Dommerholt, Jan et al., Highly accelerated inverse electron-demand cycloaddition of electron-deficient azides with aliphatic cyclooctynes, Nat Commun., 2014, 5, 1-7.
Cai, Zhengxin et al., 64Cu-Labeled Somatostatin Analogues Conjugated with Cross-Bridged Phosphonate-Based Chelators via Strain-Promoted Click Chemistry for PET Imaging: In silico through in Vivo Studies, J. Med. Chem., 2014, 57, 6019-6029.
Krantz, Allen et al., Site-Specific Labeling of a Protein Lysine Residue By Novel Kinetic Labeling Combinatorial Libraries, Comput Struct. Biotechnol. J., 2014, 9, 1-11.
Zimmerman, Erik S. et al., Production of Site-Specific Antibody-Drug Conjugates Using Optimized Non-Natural Amino Acids in a Cell-Free Expression System, Bioconjugate Chem., 2014, 25, 351-361.

* cited by examiner

COMPOSITION AND METHOD FOR MODIFYING POLYPEPTIDES

CROSS-REFERENCE TO RELATED APPLICATIONS

This application claims priority to U.S. Ser. No. 62/707,474, filed Nov. 4, 2017, and U.S. Ser. No. 62/764,086, filed Jul. 18, 2018. The contents of these applications are incorporated herein by reference in their entireties.

FIELD

The disclosure relates in general to modified proteins and methods of making and using modified proteins.

BACKGROUND

A major gap in chemical modification technologies of proteins is the lack of methods for the site-selective/chemospecific labeling of proteins at a desired site, e.g., at a lysine residue of an antibody light chain. A simple method for the site-selective labeling of the most accessible lysines in proteins would be advantageous.

SUMMARY

In an aspect, the disclosure provides a compound of Formula I

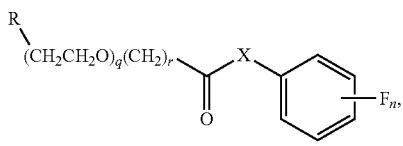

or a pharmaceutically acceptable salt thereof,
wherein
R is a reactive handle;
q is 0-40;
r is 1-20;
X is O or S or Se: and
n is 0 or 2-5.

In embodiments, the reactive handle is selected from the group consisting of an alkyne, cycloalkyne (e.g. cyclooctyne, mono- or difluorinated cyclooctyne, dimethoxyazacyclooctyne, dibenzocyclooctyne, dibenzoazacyclooctyne, biarylazacyclooctynone, bicyclononyne, 2,3,6,7-tetramethoxydibenzocyclooctyne, sulfonylated dibenzocyclooctyne, carboxymethylmonobenzocyclooctyne, mono- or difluorinated monobenzocyclooctyne, pyrrolocyclooctyne), azide, benzyl azide, 1,3-diene, nitrile oxide, nitrone, tetrazine, trans-cyclooctene or their structurally related derivatives capable of undergoing bio-orthogonal cycloaddition to an appropriate corresponding reaction entity.

In embodiments, the reactive handle is a trans-cyclooctene or tetrazine.

In embodiments, the reactive handle is an azide.

In embodiments, X is O.

In embodiments, X is S.

In embodiments, n is S.

In embodiments, the reactive handle is trans-cyclooctene or an azide, X is O, and n is 5.

In a further aspect, the disclosure provides a compound of Formula II

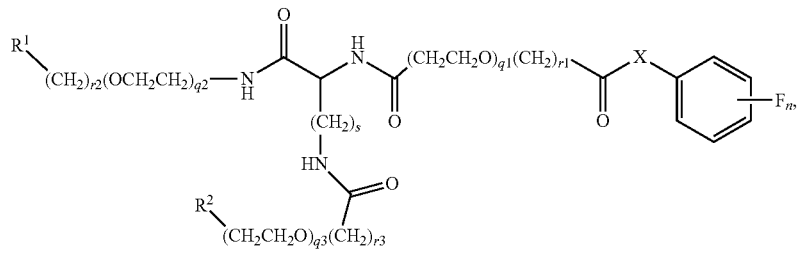

or a pharmaceutically acceptable salt thereof,
wherein
$R^1$ and $R^2$ are, each individually, a reactive handle;
q1, q2, and q3 are each, independently, 0-40;
r1, r2, and r3 are each, independently, 1-20;
s is 1-6;
X is O or S or Se: and
n is 0 or 2-5.

In embodiments, the reactive handles $R^1$ and $R^2$ are independently selected from the group consisting of an alkyne, cycloalkyne (e.g. cyclooctyne, mono- or difluorinated cyclooctyne, dimethoxyazacyclooctyne, dibenzocyclooctyne, dibenzoazacyclooctyne, biarylazacyclooctynone, bicyclononyne, 2,3,6,7-tetramethoxydibenzocyclooctyne, sulfonylated dibenzocyclooctyne, carboxymethylmonobenzocyclooctyne, mono- or difluorinated monobenzocyclooctyne, pyrrolocyclooctyne), azide, benzyl azide, 1,3-diene, nitrile oxide, nitrone, tetrazine, trans-cyclooctene or their structurally related derivatives capable of undergoing bio-orthogonal cycloaddition to an appropriate corresponding reaction entity.

In embodiments, the reactive handle is either a trans-cyclooctene or tetrazine.

In embodiments, the reactive handle of either one of $R^1$ or $R^2$, or both, is an azide.

In embodiments, X is O.

In embodiments, X is S.

In a still further aspect, the disclosure provides a linker-antibody conjugate of Formula III

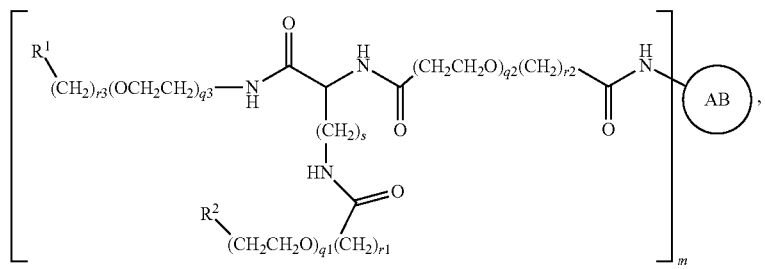

or a pharmaceutically acceptable salt thereof,
wherein
$R^1$ and $R^2$ are, each independently, a reactive handle;
q1, q2, and q3 are each, independently, 0-40;
r1, r2, and r3 are each, independently, 1-20;
s is 1-6;
m is 1-2; and
AB is an antibody.

In embodiments, the linker is site selectively attached to a lysine on AB.

In embodiments, the lysine is lysine 188.

In embodiments, the linker is between 50-100% site-selective for lysine 188.

In embodiments, the linker is between 75-100% site-selective for lysine 188.

In embodiments, the linker is at least 90% site-selective for lysine 188.

In embodiments, the reactive handles $R^1$ and $R^2$ are independently selected from the group consisting of an alkyne, cycloalkyne (e.g. cyclooctyne, mono- or difluorinated cyclooctyne, dimethoxyazacyclooctyne, dibenzocyclooctyne, dibenzoazacyclooctyne, biarylazacyclooctynone, bicyclononyne, 2,3,6,7-tetramethoxydibenzocyclooctyne, sulfonylated dibenzocyclooctyne, carboxymethylmonobenzocyclooctyne, mono- or difluorinated monobenzocyclooctyne, pyrrolocyclooctyne), azide, benzyl azide, 1,3-diene, nitrile oxide, nitrone, tetrazine, trans-cyclooctene or their structurally related derivatives capable of undergoing bioorthogonal cycloaddition to an appropriate corresponding reaction entity.

In embodiments, the reactive handle is a trans-cyclooctene or tetrazine.

In embodiments, the reactive handle is an azide.

In another aspect, the disclosure features a payload-linker-antibody conjugate of Formula IV $L^1$ and $L^2$ are linking moieties, which are the product of a click reaction;
Y and Z are each, independently, selected from a toxin, a drug, and a chelator payload; and
AB is an antibody.

In embodiments, $L^1$ and $L^2$ are the product of a click reaction between an azide and a cycloalkyne group.

In embodiments, the $L^1$ or $L^2$ group formed is the product of reacting an azide on Y or Z of Formula IV.

In embodiments, the $L^1$ or $L^2$ group formed are the product of reacting a cycloalkyne on Y and/or Z of Formula IV.

In embodiments, $L^1$ or $L^2$ are, each independently, selected from —C(O)$C_1$-$C_{30}$-heteroaromatic- or —$C_1$-$C_{30}$-heteroaromatic-C(O)—;

In embodiments, $L^1$ or $L^2$ are a linking moiety of the structure:

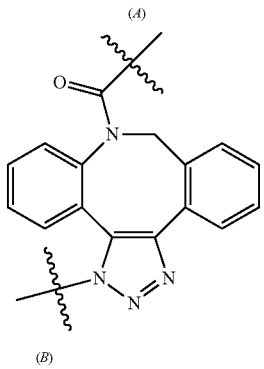

wherein either (A) or (B) are attached to the toxin, drug, or chelator payload

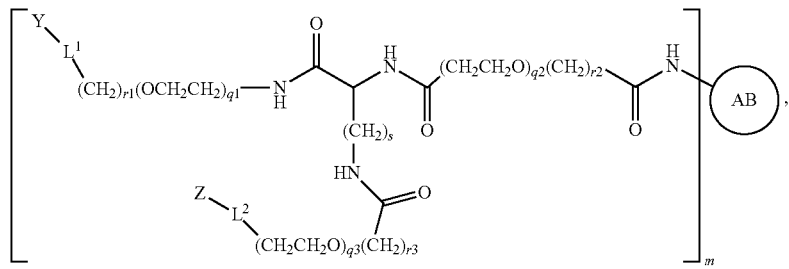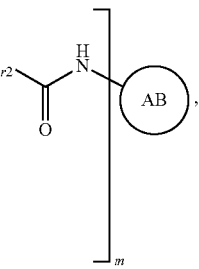

or a pharmaceutically acceptable salt thereof,
wherein
q1, q2, and q3 are each, independently, 0-40;
r1, r2, and r3 are each, independently, 1-20;
s is 1-6;
m is 1-2;

In embodiments, the linker is site selectively attached to lysine.

In embodiments, the lysine is lysine 188.

In embodiments, the linker is between 50-100% site-selective for lysine 188.

In embodiments, the linker is between 75-100% site-selective for lysine 188.

In embodiments, AB is selected from the group consisting of abciximab, adalimumab, adalimumab-atto, ado-trastuzumab emtansine, alemtuzumab, alirocumab, atezolizumab, avelumab, basiliximab, belimumab, bevacizumab, bezlotoxumab, blinatumomab, brentuximab vedotin, brodalumab, canakinumab, capromab pendetide, certolizumab pegol, cetuximab, daclizumab (Zenapax), daclizumab (Zinbryta), daratumumab, denosumab, dinutuximab, dupilumab, durvalumab, eculizumab, elotuzumab, evolocumab, golimumab, golimumab, ibritumomab tiuxetan, idarucizumab, infliximab, infliximab-abda, infliximab-dyyb, ipilimumab ixekizumab, mepolizumab, natalizumab, necitumumab, nivolumab, obiltoxaximab, obinutuzumab, ocrelizumab, ofatumumab, olaratumab, omalizumab, palivizumab, panitumumab, pembrolizumab, pertuzumab, ramucirumab, ranibizumab, raxibacumab, reslizumab, rituximab, secukinumab, siltuximab, tocilizumab, tocilizumab, trastuzumab, ustekinumab, vedolizumab, sarilumab, rituximab and hyaluronidaseguselkumab, inotuzumab ozogamicin, adalimumab-adbm, gemtuzumab ozogamicin, bevacizumab-awwb, benralizumab, and emicizumab-kxwh. trastuzumab-dkst, infliximab-qbtx, ibalizumab-uiyk, tildrakizumab-asmn, burosumab-twza, and erenumab-aooe.

In embodiments, (A) or (B) is a chelator.

In embodiments, the chelator is bound to a radionuclide.

In embodiments, the chelator is macropa or DOTA.

In embodiments, the radionuclide is actinium-225 or lutetium-177.

In embodiments, the chelator is macropa and the radionuclide is actinium-225. In embodiments, the chelator is DOTA and the radionuclide is lutetium-177.

In one aspect, the disclosure features a method for site-selectively functionalizing an amino group of a protein, comprising:

contacting the protein with an orthogonally reactive moiety comprising a compound of Formula I;

forming a covalent bond between the orthogonally reactive moiety and the amino group of the protein; and breaking the covalent bond between the orthogonally-reactive moiety and the reactive phenyl moiety (acting as a leaving group) to obtain a site-selectively functionalized (acylated) protein.

In embodiments, the protein comprises a payload.

In embodiments, the payload comprises an antibody, toxin, or chelator.

When the payload is an antibody, the antibody can be, e.g., abciximab, adalimumab, adalimumab-atto, ado-trastuzumab emtansine, alemtuzumab, alirocumab, atezolizumab, avelumab, basiliximab, belimumab, bevacizumab, bezlotoxumab, blinatumomab, brentuximab vedotin, brodalumab, canakinumab, capromab pendetide, certolizumab pegol, cetuximab, daclizumab (Zenapax), daclizumab (Zinbryta), daratumumab, denosumab, dinutuximab, dupilumab, durvalumab, eculizumab, elotuzumab, evolocumab, golimumab, golimumab, ibritumomab tiuxetan, idarucizumab, infliximab, infliximab-abda, infliximab-dyyb, ipilimumab ixekizumab, mepolizumab, natalizumab, necitumumab, nivolumab, obiltoxaximab, obinutuzumab, ocrelizumab, ofatumumab, olaratumab, omalizumab, palivizumab, panitumumab, pembrolizumab, pertuzumab, ramucirumab, ranibizumab, raxibacumab, reslizumab, rituximab, secukinumab, siltuximab, tocilizumab, tocilizumab, trastuzumab, ustekinumab, vedolizumab, sarilumab, rituximab and hyaluronidaseguselkumab, inotuzumab ozogamicin, adalimumab-adbm, gemtuzumab ozogamicin, bevacizumab-awwb, benralizumab, and emicizumab-kxwh. trastuzumab-dkst, infliximab-qbtx, ibalizumab-uiyk, tildrakizumab-asmn, burosumab-twza, and erenumab-aooe.

In come embodiments, the payload is a toxin, e.g., maytansinoid, auristatin, dolastatin, tubulysin, calicheamicin, pyrrolobenzodiazepines, doxorubicin, duocamycin, the duocarmycin derivative CC-1065, carboplatin(paraplatin), cisplatin, cyclophosphamide, ifosfamide, nidran, nitrogen mustard(mechlorethamine HCL), bleomycin, mitomycin C, cytarabine, fluorouracil, gemcitabine, trimetrexate, methotrexate, etoposide, vinblastine, vinorelbine, alimta, altretamine, procarbazine, paclitaxel, docetaxel, topotecan, irinotecan, trichothecene, an amanitin, e.g., alpha amanitin, other enediyne antibiotics, or an exotoxin, plant toxin, diphtheria toxin, botulinum toxin, tetanus toxin, dysentery toxin, cholera toxin, pyrrolobenzodiazepine, tetrodotoxin, brevetoxin, ciguatoxin, ricin, AM toxin, tubulysin, geldanamycin, maytansinoid, calicheamicin, daunomycin, doxorubicin, vindesine, SG2285, dolastatin, auristatin, cryptophycin, camptothecin, a rhizoxin, duocarmycin, an enediyne antibiotic, esperamicin, epothilone, anthracycline, taxol, carboplatinum, 5-fluoruracil, tamoxifen, calicheimycin, maytansine, tubylysin, and, analogs thereof.

In some embodiments, the payload is a chelator, e.g., 1,4,7,10-tetraazacyclododecane ([12]aneN4); 1,4,7,10-tetraazacyclotridecane ([13]aneN4); 1,4,8,11-tetraazacyclotetradecane ([14]aneN4); 1,4,8,12-tetraazacyclopentadecane ([15]aneN4); 1,5,9,13-tetraazacyclohexadecane ([16]aneN4); ethylene-diamine-tetraacetic-acid (EDTA); diethylene-triamine-penta-acetic acid (DTPA), 1,4-ethano-1,4,8,11-tetraazacyclotetradecane (et-cyclam); 1,4,7,11-tetraazacyclotetradecane (iso-cyclam); 1,4,7,10-tetraazacyclododecane-1,4,7,10-tetraacetic acid (DOTA); 2-(1,4,7,10-tetraazacyclododecan-1-yl)acetate (DO1A); 2,2'-(1,4,7,10-tetraazacyclododecane-1,7-diyl) diacetic acid (DO2A); 2,2',2"-(1,4,7,10-tetraazacyclododecane-1,4,7-triyl) triacetic acid (DO3A); 1,4,7,10-tetraazacyclododecane-1,4,7,10-tetra(methanephosphonic acid) (DOTP); 1,4,7,10-tetraazacyclododecane-1,7-di(methanephosphonic acid) (DO2P); 1,4,7,10-tetraazacyclododecane-1,4,7-tri (methanephosphonic acid) (DO3P); 1,4,8,11-15 tetraazacyclotetradecane-1,4,8,11-tetraacetic acid (TETA); 2-(1,4,8,11-tetraazacyclotetradecane-1-yl) acetic acid (TE1A); 2,2'-(1,4,8,11-tetraazacyclotetradecane-1,8-diyl) diacetic acid (TE2A); ethylene-diamine-tetraacetic-acid (EDTA), and/or Macropa, In a further aspect, the disclosure provides a site-selectively functionalized protein produced by the methods herein described.

In embodiments, the protein is provided as part of a pharmaceutical composition comprising the protein and a pharmaceutically acceptable carrier.

Also provided by the disclosure is a method of treating a condition or disease, the method comprising administering the pharmaceutical composition to a subject in need thereof.

In a further aspect, the disclosure provides a method for identifying a site-selective labeling compound, comprising;

providing a plurality of identical proteins, wherein each protein comprises two or more amino (—NH$_2$) groups;

contacting the plurality of proteins with a plurality of labeling compounds-forming a covalent attachment between one or more amino groups of one or more proteins and the first orthogonally-reactive moiety of one or more compounds, to obtain one or more labeled proteins;

identifying the protein labeled with the highest selectivity; and identifying the corresponding site-selective labeling compound.

In an embodiment, provided herein are proteins and corresponding reagents as shown in Table 1.

DETAILED DESCRIPTION

The present disclosure provides methods for site-selectively crosslinking payloads to antibodies and other proteins. This goal can be accomplished using traceless affinity labels, or alternatively, by specific acylating agents capable of high chemoselectivity, designed to label target proteins with bio-orthogonally reactive entities (ORE) using the compositions and methods described herein.

In one embodiment, the preferred target sites of this disclosure are the light chains of antibodies. The present disclosure also relates generally to systematic methods of screening a protein/antibody for site-specifically ligandable sites with proximal lysines (e.g., surface lysines), and compositions leading to such selective labeling. In this aspect the method of screening accomplishes site-selective labeling in which the affinity group is traceless, e.g., does not appear in the product, which is labeled with a bio-orthogonally reactive entity.

The present disclosure provides practical, advanced methods for the site-selective labeling of antibodies with payloads through a stepwise process that enables, first, the introduction of a bioorthogonally reactive entity such as an azide followed by reaction of a bioorthogonally reactive partner bearing any one of a large variety of payloads. The present disclosure further relates generally to the chemospecific union of antibodies with payloads through the agency of orthogonally reactive entities (ORE) that have become attached site-selectively to the antibody surface by combinatorial library methods employing esters, and the like, in a specified manner or through the use of selectively-reactive electrophiles linked to OREs. The present disclosure also relates to the characterization and use of such compositions for the purpose of augmenting or modulating the activity of the payload (e.g., biological molecule), and/or to attach a payload, e.g., polymer, drug, macromolecule, imaging agent in order to improve the safety or efficacy of the antibody, or to introduce additional activities or payloads onto the protein framework. The present disclosure generally provides methods for the site-selective modification of monoclonal and polyclonal antibodies, their fragments (e.g., Fab, F(ab')2, sdAb (single domain antibody)), bi-specific antibodies, diabodies), and the like. The modifications described herein can be used for the attachment of payloads in radio-labeling, molecular imaging, optical probes, and numerous therapeutic antibody applications, and the treatment of many disorders which include rheumatoid arthritis, bacterial and viral diseases, lupus erythematosus, psoriasis, multiple sclerosis, type-1 diabetes, Crohn's disease, and systemic sclerosis, Alzheimer disease, cancer, heart and liver disease (e.g., alcoholic liver disease), and cachexia.

Figure 1:
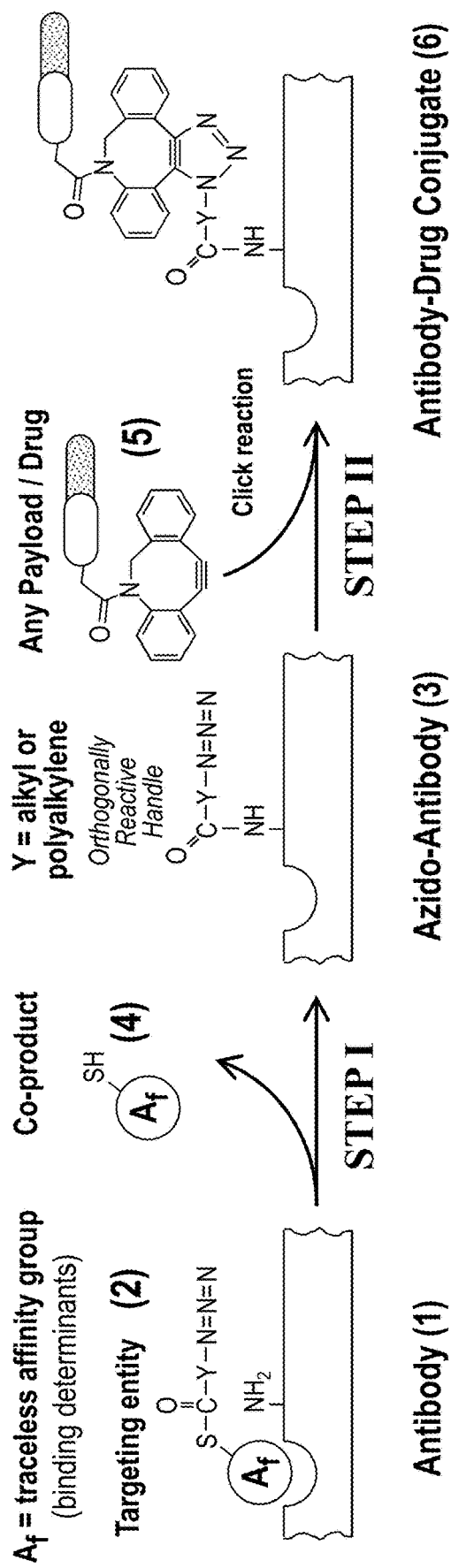
FIG. 1 depicts a method leading from a target antibody (e.g., an IgG1 isotype) to a product antibody-drug conjugate, site-selectively labeled at Lys 188.
Figure 2:
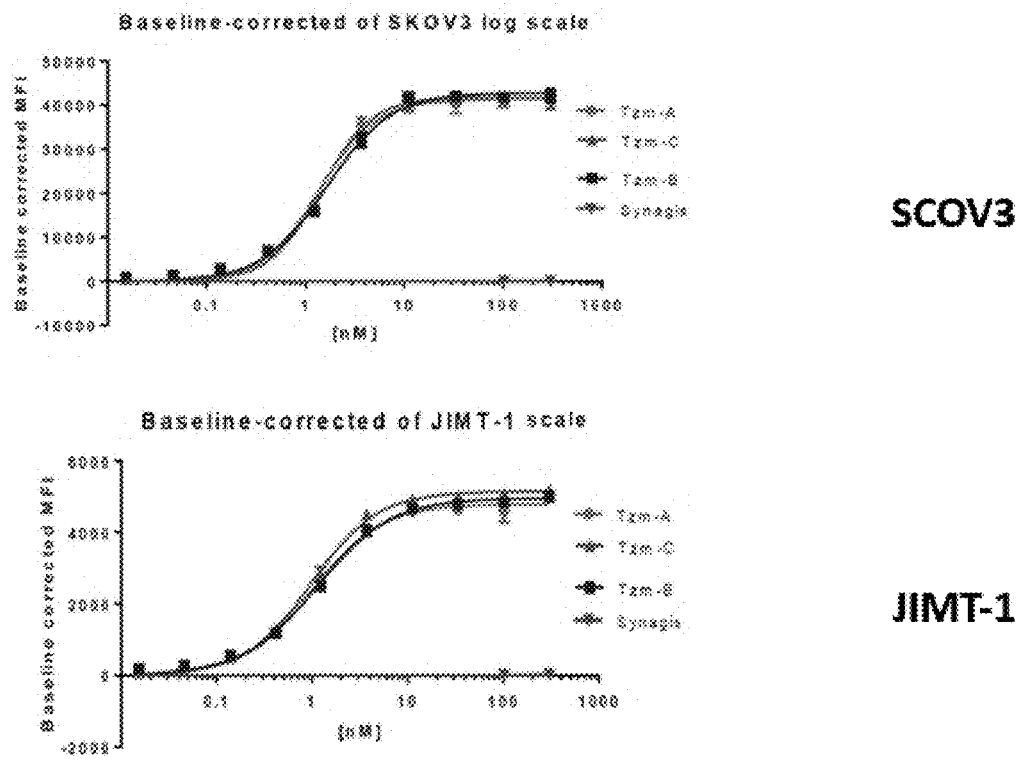
FIG. 2 shows binding curves used to determine apparent dissociation constants Kd [nM] for the tested antibody conjugates Tzm-A and Tzm-B, and the control naked antibodies Tzm-C and Palivizumab (Synagis®).

FIG. 1 illustrates a two-step method leading from a target antibody (e.g., an IgG1 isotype) to a product antibody-drug conjugate, site-selectively labeled at Lys 188.

The two-step approach can be used to synthesize antibody drug conjugates (ADC), which effect: 1. selective labeling of amines to achieve product homogeneity and chemical stability in the circulation by the simple means of amine-selective acylating agents; 2. the targeting of conserved sites of antibodies for universal applicability, and, in certain instances, 3. the innovative use of traceless affinity groups in targeting entities to standardize and simplify the modification process.

The first selective step is accomplished with an azido-linked-phenolate or thiophenolate that reacts primarily with Lys 188 of the conserved site of an antibody to be modified (FIG. 1). In some embodiments, the reaction is site selective for Lys 188. The azido group serves as a reactive handle that can be fused to DIBCO-functionalized payloads and represents a prototype that can be generalized for bioorthogonally reactive entities. For example, DIBCO-modified antibodies can be combined with azido-functionalized payloads, as representative of the repertoire of click-chemistry motifs that can be deployed to forge stable linkages between antibodies and their target payloads. This repertoire includes tetrazine/(BCN) as described in Dommerholt J. et al., *Strain-Promoted 1,3-Dipolar Cycloaddition of Cycloalkynes and Organic Azides.*, Top Curr Chem (*Cham*). 2016 April; 374 (2):16).

In the first step the OREs are expected to provide a handle for detection and assay. Their modest size and structural simplicity are major assets for scaling up quantities for producing antibody-drug conjugates.

In the second step, OREs provide a specific point of attack for the introduction of payloads that are likely to be high yield "click chemistry" reactions leading to homogeneous product. Literature precedents of conjugating payloads to proteins via azide capture by cycloalkynes emphatically support this scenario.

Among the advantages provided by the disclosure is simplified synthesis, as many OREs can be easily linked to the acylating moiety by diverse, routine synthetic methods. For OREs, a single synthetic motif can be employed, adaptable to most contingencies. Depending upon the payloads employed, synthetic methods would have to be individually tailored to implement the more complex methods utilizing payloads linked directly to the antibody framework.

Second, the use of OREs enables the construction of universal screening libraries, e.g., libraries that can be employed against any protein target, in which amino acids are randomized among a number of peptide positions to obtain highly diverse libraries. This feature is highly advantageous for globally screening a protein for site-specifically ligandable sites, and their associated ligands.

Third, screening of fully-loaded library members, each of which contain a payload, is far more expensive than using ORE's to discover the best labelers, as drugs, polymers and imaging agents and the like, are generally quite costly. Thus, this feature embodying the two-step approach to conjugates can be powerfully exploited in the context of library methodology.

Fourth, the use of ORE's introduces an element that can facilitate screens, as methods exist for the generation of optical probes from ORE's. Such optical probes provide a basis for detection of site-specific labeled entities (Fluorogenic click reaction. Le Droumaguet C, Wang C, Wang Q. Chem Soc Rev. 2010 39(4):1233-9).

Fifth, screening library members with attached payloads represents a considerable challenge as the payload must be accommodated throughout the overall conjugative process and could vitiate the specific effects of the peptide moiety (variable element) and its potential chemospecificity. ORE's, among which are alkynes and azides, are among the smallest functional groups and are unlikely to introduce significant perturbations on the intrinsic reactivities and specificities of affinity groups.

In summary, ORE-bearing libraries represent a superior motif to payload-bearing libraries as the former permit standardization of the labeling process, comprise a reactive entity for (near) quantitative attachment of payloads to proteins, and are less likely to interfere with intrinsic binding and labeling patterns of activated peptidyl groups, W.

Chemical modification of antibodies to make ADCs has to date resulted in either highly heterogeneous mixtures with amine-reactive substrates, or unstable and often toxic conjugates when cysteines are targeted. This has severely limited the development of ADCs. Homogenous ADC products, produced using site-selective strategies, have been shown to improve the therapeutic index and pharmacokinetic properties of ADCs. Current enzymatic and molecular biological approaches to achieve site-specific conjugation require re-engineering of candidate antibodies to incorporate selectively reactive residues, which makes the process time-consuming, labor-intensive and often impractical.

Since proteins contain numerous lysines, a general screen for site-specifically ligandable amines in proteins would be advantageous in a number of respects as it could provide optional, diverse sites and their associated ligands for conjugate development.

Also, it would be expedient to identify or target a limited number of sites, that might allow useful placements of linkers in combination, that do not interfere with antigen binding, given the formidable challenges of a general screen for site-specifically ligandable site discovery.

In the arena of chemical modification, conventional strategies targeting amines have generally resorted to labeling with NHS esters and the like to achieve stable amide linkages. The drug Kadcyla is the heterogeneous product of such an approach which contains numerous lysine adducts. Although NHS esters are regarded as indiscriminant acylating agents, Weil has shown that if they are added in small increments to proteins, lysines can be modified site-specifically, albeit in proteins containing a limited number of lysines, but the process is not scalable. Recently, Dovgan et al., (*Acyl Fluorides: Fast, Efficient, and Versatile Lysine-Based Protein Conjugation via Plug-and-Play Strategy*, Bioconjugate Chem. 2017, 28, 1452-1457) reported that a small molecule acylating agent, an acid fluoride, can label antibody lysines in a controlled way, but no selectivity data was presented. Hacker et al. (Global profiling of lysine reactivity and ligandability in the human proteome, Nature Chemistry), have tested a number of active esters for global profiling of lysines and has identified numerous residues with heightened reactivity that are enriched at protein functional sites. Despite the enormous number of acylating agents that can be envisioned, little is known about their selectivity patterns with proteins/antibodies. It would be highly advantageous to identify structurally simple molecules that can be used to selectively modify antibodies because of their low cost and ease by which they can be scaled in manufacturing processes.

This disclosure highlights our discovery that acyl transfer agents of minimal structure bearing "clickable" entities such as azide ($N_3$) in linear as well as branched chain configurations are capable of selectively modifying IgG antibodies and afford access to selectively-labeled ADCs bearing diverse payloads.

The payload may be a compound which allows the diagnostic visualization of specific sites or compartments within the body by employing such diagnostic techniques as positron emission tomography (PET), computerized tomography (CT), single photon emission computerized tomography (SPECT), magnetic resonance imaging (MRI), nuclear magnetic imaging (NMI), fluoroscopy, ultrasound, X-ray radiography, endoscopy designed to produce images, such as electroencephalography (EEG), magnetoencephalography (MEG), electrocardiography (ECG), and others represent other applicable techniques).

For such applications, the payload can comprise such imaging agents as contrast agents, radioisotopes of such elements as iodine (I), including $^{123}I$, $^{125}I$, $^{131}I$, etc., barium (Ba), gadolinium (Gd), technetium (Tc), including $^{99}Tc$, phosphorus (P), including $^{31}P$, fluorine (F) including [19]-F, iron (Fe), manganese (Mn), thallium (Tl), chromium (Cr), including $^{51}Cr$, carbon (C), including $^{11}C$, or the like, fluorescently labeled compounds, etc. Such ORE bearing payloads are also useful for labeling molecules in a mixture, where the target molecule has been pre-labeled by the complementary reaction partner.

Optical agents such as fluorescent, and UV-Vis probes and well as Near Infrared Dyes are potential payloads.

In yet another application, the payload may be chosen such that it functions to sterically hinder or alter the binding specificity of a specific target binding protein. Such entities may take many forms which are readily determinable by those skilled in the art, and include various chemical groups which have affinities for functional sites on the protein. Such payloads may also comprise amino acids, structures which themselves serve to provide binding affinity for a target molecule, much like biotin, or the like. Such payloads find use, for example, in inhibiting the ability of a binding protein to bind to its protein target and for inactivating cell membrane proteins, such as channels, enzymatic proteins, specific receptors, and the like. Such payloads may also serve a research purpose, for example, in allowing the dissection of the function of a variety of surface membrane proteins or for the identification and/or purification of the labeled target molecule.

In still another application the payload may be chosen to improve the pharmacokinetics of a drug, e.g., by increasing its duration of action, decreasing its immunogenicity, and/or its rate of metabolism. Such payloads may take several forms, which include polymers, such as polyethylene glycol and polysialic acid polymers and various proteins such as human serum albumin that serve to maintain high levels in the circulation by limiting excretion in the glomerulus.

In yet another application, the payload may be a companion protein that forms homo- or hetero-dimers that are more active than individual monomers and/or provide multiple biological activities useful in therapeutic applications.

In yet another application the payload may be a drug or toxin that provides an antibody-drug conjugate of therapeutic utility.

In still other applications the payload or the ORE-labeled protein may be an antibody that serves to deliver the attached component to a target cell for therapeutic reasons as in the case of antibody-drug conjugates.

In yet another application the payload or ORE-labeled protein may be an annexin protein that serves to deliver entities to regions of elevated apoptosis for therapeutic benefit.

In each of the above applications, covalent bonding of the payload to the acceptor ORE-labeled protein serves to augment or add biological functions to the target molecule containing its reaction partner. Thus, by employing the subject compositions, one may modify the nature of the target molecule, change the characteristics of the target molecule, allow for the identification and/or isolation of the target molecule, etc.

The variable element will be bonded to the orthogonally reactive entity (ORE) through a unit, which will comprise a chemically reactive function (e.g., thioester) which will react with a reactive functionality (e.g., amino) at the target protein site to form a covalent bond. Covalent bond formation at the target protein, in turn, results in covalently bonding the ORE to the target site with concomitant liberation of the variable element.

The compositions of the disclosure will include a reactive functionality, containing —S—CO—R—, —O—CO—R, —O—CS—R, —O—CSe—R, —S—R—CH$_2$—, —O—R—CH$_2$, where R is aryl or alkyl. The reactive functionality will generally be stable in an aqueous environment within the timeframe of the first reaction and will usually contain an acyl group, or an imidate, thereby being capable of forming a covalent bond with an amino group of the target protein, to give an amide or amidine derivative. For the most part, the reactive acyl transfer agents will be thiol- or oxygen-esters and involve phenolic or thiophenolic compounds, or be alkyl esters, and the like.

The composition of the disclosure may include a linker between the ORE and the variable element. The linker can be selected for a desired characteristic e.g., water solubility, reduced non-specific binding, and/or a group bonded to the reactive functionality to provide an ester, thioester, imidate, thioimine, or the like. For the most part, the linker, when other than a single bond, will have from about 1-30 carbon atoms, and from about 0-10, more usually 1-8 heteroatoms, which for the most part will be O, N, Se, and S. The particular linker's selection is based on the nature of ORE and the variable structural group and will be designed to provide convenient characteristics for deployment of the molecule in the context of the relevant biological milieu. Of particular interest, where a linker atom constitutes part of the reactive functionality, is to have an aromatic derivative, so that the heteroatom of the reactive functionality is bonded directly to an aromatic carbon atom. Alternatively, one may exploit non-aryl thioesters and the like, using linker chains that contain alkylene or alkyleneoxy.

The linker may have various functions: to control the reactivity of the fragment electrophile; to provide for enhanced water solubility; by providing for a useful linking group between the ORE and the fragment electrophile. In embodiments, the linker comprises from about 1-50, e.g., 20, carbon atoms in the chain, which atoms may be carbon, nitrogen, oxygen, sulfur, selenium, and the like. The linker may contain alkylene groups, generally of from 2-16, more usually of from 1-25 carbon atoms, polyoxyalkylene groups, where the alkylene groups will be of 1-3 carbon atoms, and having from 1-30 more usually of from about 1-16 or 1-8 units, an amino acid, including alpha and omega amino acids, or oligopeptide having from 1-8, usually 1-6 amino acids, where the amino acids may be polar or non-polar, charged or uncharged, aliphatic, alicyclic, aromatic or heterocyclic, naturally occurring or synthetic.

As is evident from the above, the various units of the ultimate rapid labeling agents to be employed as the first labeling molecules will be selected for compatibility, particularly to impart stability in the case of library components.

For identification of selectively labeled amino groups of the protein target, peptide mapping techniques including quantitative LC-MS methodologies will be employed.

Implementation of Mass Spectrometry (MS) as a detection method allows for simultaneous data collection on the labeling status of the protein, directly. MS screens we have invented deliver rapid information on the extent of labeling of the target protein and provide rapid and unambiguous determination of the entity responsible for labeling.

The subject products, which comprise payloads crosslinked to proteins, when administered physiologically, can be administered as a bolus, but may be introduced slowly over time by transfusion using metered flow, or the like. Alternatively, although less preferable, blood may be removed from the host, contacted with the affinity label compound ex vivo, and returned to the host. However, the method of administration is dependent upon the particular application and may depend upon the locus of action and pharmaceutic properties of the payload or protein. The crosslinked products will be administered in a physiologically acceptable medium, e.g., deionized water, phosphate buffered saline, saline, mannitol, aqueous glucose, alcohol, vegetable oil, or the like. Usually, a single injection will be employed although more than one injection may be used, if desired. The crosslinked products may be administered by any convenient means, including syringe, catheter, or the like. The particular manner of administration will vary depending upon the amount to be administered, whether a single bolus, sequential, or continuous administration, or the like. Administration will often be intravascular, where the site of introduction is not critical to this disclosure, preferably at a site where there is rapid blood flow, e.g., intravenously, peripheral or central vein. The intent is that the compound administered be effectively distributed in the vascular system so as to be able to react with target molecules therein.

The dosage of the crosslinked product will depend upon the specific entity being employed and will, therefore, be dependent on the adverse effects of the entity of interest, if any, the indication being sought, the sensitivity of the compound to destruction by vascular components, the route of administration, and the like. As necessary, the dosage of the crosslinked product may be determined empirically, initially using a small multiple of the dosage normally administered, and as greater experience is obtained, enhancing the dosage. Dosages will generally be in the range of 1 ng/Kg to 10 mg/Kg, usually being determined empirically in accordance with known ways, as provided for in preclinical and clinical studies.

Targeted Kinetic Labeling Libraries and Traceless Affinity Labels

The foregoing description is based on the use of single reagents to treat antibodies, or libraries in which the affinity element contains only oligomeric functionality and there is essentially no information about ligands to the target protein. Such libraries are constructed by randomizing amino acids among the several variable positions and are "universal" kinetic labeling libraries in that they represent unbiased first line screens of proteins. When binding determinants to specific sites are available it is expedient to incorporate, or build on, such known affinity (peptidyl or non-peptidyl) elements in the library. By making them a constant feature of the affinity group in combination with variable (e.g., peptidyl) elements, the libraries are essentially targeted and biased toward targeted protein sites. In this scenario, the overall complexity of the combinatorial library may be reduced while the affinities of library members for the protein target are enhanced.

For example, small peptides have been reported to bind to the Fc fragment of antibodies with high affinity ($K_d$=0.5 nM, Tsai et al., Anal. Chem, 2014, 86, 2931-8). This RRGW peptide can form the basis for extensions that build on the tetrapeptide framework to give longer peptides (e.g., RRGWXXXX) of high affinity that can carry reactive entities of kinetic labeling libraries described herein.

Reformatted or Re-Engineered Affinity Labels

A characteristic feature of kinetic labeling libraries is that the entities conjugated to the target protein are derived from traceless linkers (or alternatively traceless affinity labels). This feature is of the utmost importance to labeling in that it allows for the presence of widely diverse binding determinants in the affinity label, which do not appear in the conjugated protein. This design element provides a significant advantage over approaches which lead to the retention of binding determinants which often are quite complex, and tantamount to extraneous elements with neither a functional role nor desirable properties.

Consequently, this disclosure can be adapted through innovative reformatting of an affinity label which hitherto conjugates binding determinants to the target protein.

Definitions

The term "affinity label" is used herein broadly to describe molecules that are composed of an affinity group linked to an entity that is potentially reactive with proteins or other macromolecules. The affinity group (naturally or fortuitously) possesses binding determinants primarily for a specific site on a protein or other macromolecule that enables selective labeling of a proximal group on the protein surface.

As used herein, the term "electrophilic moiety" refers to molecule that is attracted to electrons. Such electrophilic moieties are capable of reacting with nucleophiles, such as amino groups of proteins and peptides. Preferred embodiments of electrophilic moieties include —C(O)O—, —C(O)S—, —C(O)Se—, —SO$_2$O—, —SO$_2$S— and —SO$_2$Se—.

As used herein, the term "alkyl or alkanoyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl.

The term "alkenyl," alone or in combination refers to a straight-chain, cyclic or branched hydrocarbon residue comprising at least one olefinic bond and the indicated number of carbon atoms. Preferred alkenyl groups have up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl, isobutenyl, 1-cyclohexenyl, 1-cyclopentenyl.

The term "alkynyl" includes unsaturated aliphatic groups analogous in length to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

The term antibody as used herein may refer to monoclonal and polyclonal antibodies, their fragments (e.g., Fab, F(ab')$_2$, scFv (single-chain variable), sdAb (single domain antibody)), bi-specific antibodies, diabodies), and the like.

The term "aryl" includes aromatic monocyclic or multicyclic e.g., tricyclic, bicyclic, hydrocarbon ring systems consisting only of hydrogen and carbon and containing from six to nineteen carbon atoms, or six to ten carbon atoms, where the ring systems can be partially saturated. Aryl groups include, but are not limited to, groups such as phenyl, tolyl, xylyl, anthryl, naphthyl and phenanthryl. Aryl groups can also be fused or bridged with alicyclic or heterocyclic rings which are not aromatic so as to form a polycycle (e.g., tetralin).

The term "bioorthogonal" or "orthogonal" refers to any chemical reaction that can occur inside of living systems without interfering with native biochemical processes and hence would not occur with biological molecules such as proteins under conditions of physiological temperatures and pH. The term orthogonal is used interchangeably herein with bioorthogonal in the context of reactivity, as is reactive handle. These terms are meant to indicate that (bio)orthogonally reactive entities are click chemistry-reactive, but inert to reactions with biochemicals.

The term "chemoselectivity" refers to the preferential reaction of a chemical reagent with one of two or more similar functional groups.

The term "chemospecificity" refers to a reaction in which only one of a number of similar functional groups is modified.

The term "click chemistry" is used as defined in *Click Chemistry: Diverse Chemical Function from a Few Good Reactions*, H. C. Kolb, M. G. Finn and K. B. Sharpless, *Angew. Chem. Int. Ed.*, 2001, 40, pp. 2004-2021 and includes alkynes, cycloalkynes such as cyclooctynes and cyclononynes e.g. bicyclo[6.1.0]non-4-yn-9-ylmethanol), trans-cyclooctene, nitrones, nitrile oxides, azides and the like. In particular, the click chemistry used herein preferably uses a strained alkyne in order to avoid the use of a copper catalyst. The term "click chemistry" can also mean [3+2] cycloadditions, thiol-ene reactions, diels-alder reaction, [4+1] cycloadditions, and nucleophilic reactions on strained rings.

As used herein, the phrase "product of a click reaction" refers to the end product of click chemistry as defined above. In particular, the products can include 1,4-disubstituted triazole, 1,5-disubstituted triazole, 1,4,5-trisubstituted triazole, diels-alder type olefins, and thiol-ene products. Preferably, the products include 1,4,5-trisubstituted triazole, including

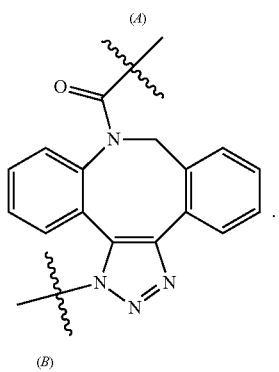

Examples of cyclooctynes suitable for click reactions are provided in Dommerholt et al. Top Curr Chem (Z) (2016) 374:16 and include OCT cyclooctyne, MOFO monofluorinated cyclooctyne, DIFO difluorocyclooctyne, DIMAC dimethoxyazacyclooctyne, DIBO dibenzocyclooctyne, DIBAC dibenzoazacyclooctyne, BARAC biarylazacyclooctynone, BCN bicyclononyne, TMDIBO 2,3,6,7-tetramethoxy-DIBO, S-DIBO sulfonylated DIBO, COMBO carboxymethylmonobenzocyclooctyne, and PYRROC pyrrolocyclooctyne.

The term "conjugate" refers to a chemical compound that has been formed by the joining of two or more entities.

The term "conserved sequence" refers to a base sequence in a DNA molecule (or an amino acid sequence in a protein) that has remained essentially unchanged, and so has been conserved, throughout evolution. Conserved sites (also referred to as consensus binding sites) are thus an evolutionary consequence of unchanged sequences or those with closely similar homology and thus generally have similar affinities.

The term "cycloaddition" refers to a pericyclic chemical reaction, in which two or more unsaturated molecules (or parts of the same molecule) combine with the formation of a cyclic adduct in which there is a net reduction of the bond multiplicity.

The term "drug" as used herein, means a pharmaceutical formulation containing at least one pharmaceutically active compound. In one embodiment the pharmaceutically active compound has a molecular weight up to 1500 Da and/or is a peptide, a protein, a polysaccharide, a vaccine, a DNA, an RNA, an enzyme, an antibody or a fragment thereof, a hormone or an oligonucleotide, or a mixture of the above-mentioned pharmaceutically active compound.

The term "heteroaryl," as used herein, represents an aromatic (i.e., containing 4n+2 pi electrons within the ring system) mono-, bi-, or tricyclic-membered ring having between 5-14 ring members and containing one, two, three, or four heteroatoms independently selected from the group consisting of nitrogen, oxygen, and sulfur. Exemplary heteroaryls include, but are not limited to pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl (e.g., 1,3,4-thiadiazole), isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, purinyl, thiadiazolyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like.

The term "orthogonally reactive entity" (ORE) or "orthogonally reactive moiety" is used (1) herein to distinguish its mutually exclusive chemical reactivity from the chemical reactivity of biological functionality under laboratory or physiological conditions, and (2) as it applies to click chemistry reactions to which biological polymers are inert. Preferred examples of orthogonally reactive entities include an alkyne, cycloalkyne, azide, 1,3-diene, nitrile oxide, nitrone, tetrazine, and trans-cyclooctene.

The term "reactive handle," as used herein, refers to a reactive moiety that can partake in a bond-forming reaction under physiological conditions. Examples of suitable reactive handles are, for example, chemical moieties that can partake in a click chemistry reaction (see, e.g., H. C. Kolb, M. G. Finn and K. B. Sharpless (2001). Click Chemistry: Diverse Chemical Function from a Few Good Reactions. Angewandte Chemie International Edition 40 (11): 2004-2021). Some suitable reactive handles are described herein and additional suitable reactive handles will be apparent to those of skill in this art, as the present disclosure is not limited in this respect. Unless indicated differently, the terms reactive handle and bio-orthogonal reactive entity are used interchangeably herein.

The term "payload" refers to any moiety that has potential commercial or medicinal value.

Examples of payloads include imaging moieties, antibodies, antibody fragments, proteins, optical agents, vitamins, enzymes, peptides, peptoids, toxins, drugs, prodrugs, ligands to a biomarker, stimulators of efferocytosis, compounds targeting a receptor selected from the group consisting of folate, EGFR, ALK, MET, PTK7 and KRAS or any oncogene product, anthracyclines, taxols, auristatins, amanitin, camptothecin, bleomycim, carboplatinums, cytarabine, 5-fluoruracil, tamoxifen, calicheimycin, maytansine, tubylysin, etoposide, duocarmycin derivatives such as CC-1065, duocarmycin and esperamicin, a folate, pyrrolobenodiazepine and an RGD linked moiety.

The term "peptoids" are defined as poly-N-substituted glycans that act as peptidomimetics and are resistant to preoteolysis.

The term "efferocytosis" refers to the process by which dying/dead cells are removed by phagocytosis. A "stimulator of efferocytosis" is any compound that promotes the process of efferocytosis. The term "subject" is intended to include organisms, e.g., prokaryotes and eukaryotes, which are capable of suffering from or afflicted with a disease, disorder or condition. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer, an autoimmune disease, arthritis, atherothrombosis, or plaque rupture. In another embodiment, the subject is a cell.

The term "peptide" includes chains of amino acids linked by peptide bonds. The term "peptide" can also refer to a "protein" or "polypeptide" (e.g., annexin proteins, granulocyte macrophage colony-stimulating factor, human superoxide dismutase, leptin, myoglobin, albumin, avidin, and an enzyme), which are compounds made of amino acids arranged in a linear chain and folded into a globular form. A variety of polypeptides or proteins may be used within the scope of the methods and compositions provided herein. In certain embodiments, the proteins may comprise antibodies or fragments of antibodies containing an antigen-binding site. As used herein, a protein, polypeptide or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide" are used interchangeably herein. In certain contexts, the protein may represent any macromolecule containing amines or thiols. Accordingly, the term "protein or peptide" encompasses amino acid sequences comprising at least one of the common amino acids found in naturally occurring proteins, or at least one modified or unusual amino acid. Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The protein, polypeptide and peptide sequences can be found at computerized databases known to those of ordinary skill in the art. One such database is the National Center for Biotechnology Information's Genbank and GenPept databases. Alternatively, various commercial preparations of proteins, polypeptides, and peptides are known to those of skill in the art.

In some embodiments, "physiological pH" refers to a pH of 7-8, 7.2-7.6, 7.3-7.5 or 7.35-7.45. In some embodiments, "physiological temperature" refers to 36-38° C. or 36.5-37.5° C.

The term "pharmaceutical composition" as used herein, represents a composition containing a compound described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers to any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "prevent," as used herein, refers to prophylactic treatment or treatment that prevents one or more symptoms or conditions of a disease, disorder, or conditions described herein. Preventative treatment can be initiated, for example, prior to ("pre-exposure prophylaxis") or following ("post-exposure prophylaxis") an event that precedes the onset of the disease, disorder, or conditions. Preventive treatment that includes administration of a compound described herein, or a pharmaceutically acceptable salt or solvate thereof, or a pharmaceutical composition thereof, can be acute, short-term, or chronic. The doses administered may be varied during the course of preventative treatment.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

Where a group is substituted, the group may be substituted with 1, 2, 3, 4, 5, or 6 substituent groups. Optional substituent groups include, but are not limited to: $C_{1-6}$ alkyl, $C_{2-6}$ alkenyl, $C_{2-6}$ alkynyl, aryl, heteroaryl, halogen (—F, —Cl, —Br, or —I), azido (—N$_3$), nitro (—NO$_2$), cyano (—CN), acyloxy (—OC(=O)R'), acyl (—C(=O)R'), alkoxy (—OR'), amido (—NR'C(=O)R" or —C(=O)

NRR'), amino (—NRR'), carboxylic acid (—CO$_2$H), carboxylic ester (—CO$_2$R'), carbamoyl (—OC(=O)NR'R" or —NRC(=O)OR'), hydroxy (—OH), isocyano (—NC), sulfonate (—S(=O)$_2$OR), sulfonamide (—S(=O)$_2$NRR' or —NRS(=O)$_2$R'), or sulfonyl (—S(=O)$_2$R), where each R or R' is selected, independently, from H, C$_{1-6}$ alkyl, C$_{2-6}$ alkenyl, C$_{2-6}$ alkynyl, aryl, or heteroaryl. In some embodiments, the substituent groups themselves may be further substituted with, for example, 1, 2, 3, 4, 5, or 6 substituents as defined herein. For example, a C$_{1-6}$ alkyl, phenyl, or heteroaryl group may be further substituted with 1, 2, 3, 4, 5, or 6 substituents as described herein.

The present disclosure includes all isomeric (e.g., enantiomeric, diastereomeric, and geometric (or conformational)) forms of the compounds; for example, syn and anti isomers, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds are also encompassed by the disclosure.

The present disclosure includes all pharmaceutically acceptable isotopically-labeled compounds of same, wherein one or more atoms are replaced by atoms having the same atomic number, but an atomic mass or mass number different from the atomic mass or mass number usually found in nature. Examples of isotopes suitable for inclusion are isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Salts derived from appropriate bases include alkali metal, alkaline earth metal, and ammonium salts. Representative alkali or alkaline earth metal salts include sodium, lithium, potassium, calcium, magnesium, and the like. One class of salts includes the pharmaceutically acceptable salts. The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "pharmaceutically acceptable solvate" as used herein means a compound as described herein wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the molecule is referred to as a "hydrate."

As used herein, "site-specific" refers to a reaction or transformation (e.g., the acylation of a protein) wherein a single product (e.g., acylation of a particular basic residue of a protein) comprises about 100%, at least about 90%, or at least about 80% of all products formed.

As used herein, "site-selective" refers to a reaction or transformation (e.g., the acylation of a protein) wherein the most-abundant product (e.g., acylation of a particular basic residue of a protein) comprises at least about 70%, at least about 60%, at least about 50%, at least about 40%, at least about 30%, or at least about 20% of all products formed, and wherein the ratio of the most-abundant product to the next most-abundant product is in the range of about 1.1:1 to about 1000:1. In a particular embodiment, the ratio of the most-abundant product to the next most-abundant product is in the range of about 2:1 to 100:1. In another particular embodiment, the ratio of the most-abundant product to the next most-abundant product is about 10:1.

The terms "traceless linkers" and "traceless affinity labels" are used interchangeably herein to refer to reactions with target molecules, e.g., proteins. Traceless linkers or traceless affinity labels are so called herein because an examination of the site-selectively conjugated product reveals no trace of binding determinants that facilitated the linking reaction.

In an embodiment, the disclosure provides antibodies conjugated to an orthogonally reactive entity (ORE) and linked predominantly to antibody light chains via acyl transfer reactions. For example, entities comprising an azido-alkanoyl or azido-polyalkyleneoxy moiety, covalently linked to an antibody light chain, and will reflect the general approach with ORE's in subsequent descriptions herein for purposes of exposition.

Included in the disclosure are compounds comprising electrophiles linked via PEG or non-PEG moieties to azide moieties capable of acyl transfer that can selectively modify antibodies. The conjugates and crosslinked products themselves are useful in many respects including molecular diagnostic and therapeutic applications.

Also provided are methods of contacting target antibodies with such acyl transfer agents to covalently link azido groups preferentially to a desired target, e.g. an antibody light chains, as well as the compositions of the conjugates resulting from such methods. Also provided are methods for producing antibody-drug conjugates integrating the foregoing methodology in a two-step sequence culminating with click chemistry. The disclosure further provides methods of treating, preventing, or ameliorating a disease, disorder or condition in a mammal comprising administering a therapeutically effective amount of a therapeutic antibody drug conjugate of the disclosure.

In an embodiment, the present disclosure relates to a method for site-selectively functionalizing an amino group of a protein, comprising:

contacting the protein with any one of the compounds disclosed herein;

forming a covalent attachment between the amino group of the protein and orthogonally-reactive moiety of the compound; and breaking the covalent attachment between the first orthogonally-reactive moiety and the leaving group of the labeling compound, to obtain a site-selectively functionalized protein.

In an embodiment of the method, the first orthogonally-reactive moiety comprises an azide.

In an embodiment, the protein is an antibody and the amino group is located in the Fab region of the antibody. In an embodiment, the antibody is a therapeutic antibody useful for the treatment of cancer or autoimmune diseases.

In an embodiment, the compound has an affinity for a conserved region of the protein.

In an embodiment, the affinity is represented by a Kd of 100 μM or less.

In an embodiment, the method further comprises:

contacting the site-selectively functionalized protein linked to an ORE with a payload compound, wherein the payload compound comprises a second orthogonally-reactive moiety; and forming one or more covalent bonds between the first orthogonally-reactive moiety and the second orthogonally-reactive moiety.

In an embodiment, the first orthogonally-reactive moiety comprises an azide, and wherein the second orthogonally-reactive moiety comprises an alkyne or cycloalkyne.

In an embodiment, the payload compound is an imaging moiety, antibody, antibody fragment, protein, optical agent, vitamin, enzyme, peptide, peptoid, toxin, drug, prodrug, ligand to a biomarker, or stimulator of efferocytosis, a radionuclide chelator.

In an embodiment, the payload compound targets a receptor selected from the group consisting of folate, EGFR, ALK, MET, PTK7 and KRAS or any oncogene product.

In an embodiment, the payload compound is selected from the group of: anthracyclines, taxols, auristatins, amanitins, camptothecin, bleomycim, carboplatinums, cytarabine, 5-fluoruracil, tamoxifen, calicheimycin, maytansine, tubylysin, etoposide, duocarmycin derivatives such as CC-1065, analogs, duocarmycin and esperamicin, a folate, pyrrolobenodiazepine and an RGD linked moiety.

In an embodiment, the payload compound is selected from the group consisting of radio-labels, molecular imaging agents, optical probes, nucleotides, oligosaccharides, and polymers.

In an embodiment, the forming of one or more covalent bonds between the first orthogonally-reactive moiety and the second orthogonally-reactive moiety occurs at physiological temperature and pH.

In an embodiment, the physiological temperature is 0-50° C., and the physiological pH is 5-9.

In an embodiment, the forming of one or more covalent bonds between the first orthogonally-reactive moiety and the second orthogonally reactive moiety occurs at around 0° C.

In an embodiment, the forming of one or more covalent bonds between the second orthogonally reactive moiety and the payload occurs at around 15° C. to 100° C.

In an embodiment, the forming of one or more covalent bonds between the first orthogonally-reactive moiety occurs at around 0° C. and the second orthogonally-reactive moiety In an embodiment, the forming of one or more covalent bonds between the In another aspect, provided herein is a method for discovering site-selectively ligandable sites and their complementary ligands, comprising;

providing a plurality of identical proteins, wherein each protein comprises two or more amino ($-NH_2$) groups;

contacting the plurality of proteins with a plurality of labeling compounds independently selected from the compound according to the present disclosure;

forming a covalent attachment between one or more nucleophilic groups of one or more proteins and the first orthogonally-reactive moiety of one or more compounds, to obtain one or more labeled proteins;

identifying the protein labeled with the highest selectivity; and identifying the corresponding site-selective labeling compound.

In an embodiment, the method further comprises identifying the protein labeled with the highest selectivity and in the highest yield.

In another aspect, the disclosure provides a method for discovering site-selectively ligandable sites and their complementary ligands, comprising;

providing a plurality of identical proteins, wherein each protein comprises two or more amino ($-NH_2$) groups;

contacting the plurality of proteins with a plurality of labeling compounds independently selected from the compound according to the present disclosure;

forming a covalent attachment between one or more nucleophilic groups of one or more proteins and the first orthogonally-reactive moiety of one or more compounds, to obtain one or more labeled proteins; and identifying the labeling compounds incorporating the greatest amount of label, and their preferred sites of attachment.

In an embodiment, the site-selective labeling compound is identified using click chemistry reactions in conjunction with ELISA technology to monitor the extent of incorporation of the first orthogonally-reactive moiety in the target protein.

In an embodiment, the site-selective labeling compound is identified using click chemistry reactions in conjunction with fluorescent labeling technology to monitor the extent of incorporation of the first orthogonally-reactive moiety in the target protein.

In an embodiment, the protein is an antibody. In an embodiment, the antibody is a therapeutic antibody useful for the treatment of cancer or autoimmune diseases.

In an embodiment, the nucleophilic groups are amino groups. In an embodiment, amino groups are located in the Fab region of the antibody.

In an embodiment, the labeling compound has an affinity for a conserved region of the protein.

In another embodiment the labeling compound has the structure of formula (I):

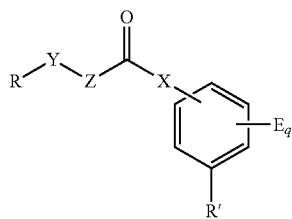

wherein

E is a moiety selected from the group consisting of halogen, —CN, —NO$_2$, —SO$_2$, —SO$_2$NH$_2$, —S(O)$_2$C$_1$-C$_6$ alkyl, —S(O)$_2$aryl, —SO$_3$H and —OC$_1$-C$_6$ alkyl;

X is O, S or Se;

Y is a linker selected from the group consisting of alkyl, polyalkylenoxide, and combinations thereof, for example Y has the formula: —(CH$_2$CH$_2$O)$_m$(CH$_2$)$_n$—, wherein m is 0-30 and n is 1-20;

R is selected from the group consisting of an alkyne, cycloalkyne, azide, 1,3-diene, nitrile oxide, nitrone, tetrazine, and trans-cyclooctene; and R' is absent or is —C(O)OH, —C(O)OC$_1$-C$_6$ alkyl, —C(O)NH$_2$, —C(O)NHC$_1$-C$_6$ alkyl, —C(O)N(C$_1$-C$_6$ alkyl)$_2$, —SO$_2$NH$_2$, —SO$_3$H, —SO$_2$NHC$_1$-C$_6$ alkyl, —SO$_2$N(C$_1$-C$_6$ alkyl)$_2$, nitro, cyano, or halogen;

q is 0, 1, 2 3 or 4;

Z is absent or is R"N—, R"=H, alkyl, aryl

In another embodiment the labeling compound has the formula (II):

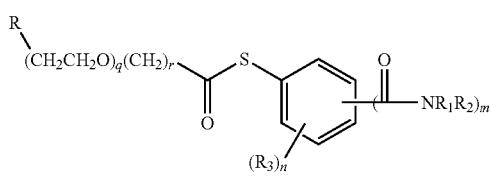

wherein

R is selected from the group consisting of an alkyne, cycloalkyne, azide, 1,3-diene, nitrile oxide, nitrone, tetrazine, and trans-cyclooctene;

R$_1$ is hydrogen or C$_1$-C$_6$-alkyl;

R$_2$ is hydrogen or C$_1$-C$_6$-alkyl;

R$_3$ is an electron-withdrawing group; and q is 0-100; r is 1-20; m is 0-1; and n is 0-4.

In a particular embodiment the labeling compound has the formula (III)

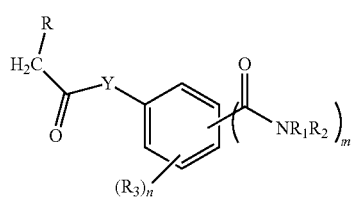

wherein

R is selected from the group consisting of an alkyne, cycloalkyne, azide, 1,3-diene, nitrile oxide, nitrone, tetrazine, and trans-cyclooctene;

R$_1$ is hydrogen or C$_1$-C$_6$-alkyl;

R$_2$ is hydrogen or C$_1$-C$_6$-alkyl;

R$_3$ is an electron-withdrawing group, e.g., a moiety selected from the group consisting of halogen, —CN, —NO$_2$, —SO$_2$, —SO$_2$NH$_2$, —S(O)$_2$C$_1$-C$_6$ alkyl, —S(O)$_2$ alkyl, —SO$_3$H and —OC$_1$-C$_6$ alkyl; Y is O, S or Se; and m is 0-1; and n is 0-5.

In another aspect, provided herein is a compound of formula (IV):

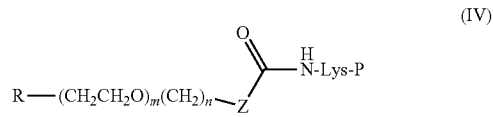

wherein

P is a protein;

Lys is a lysine residue in P;

R is a moiety selected from the group consisting of an alkyne, cycloalkyne, azide, 1,3-diene, nitrile oxide, nitrone, tetrazine, and trans-cyclooctene); Z is absent or is R'N—, R'=H, alkyl, aryl or heteroaryl; m is 0-40; and n is 1-20.

In an embodiment, P is an antibody.

In another aspect embodiment, provided herein is a compound of formula (V):

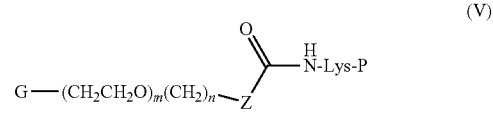

wherein

P is a protein;

Lys is a lysine residue in P;

G is a moiety comprising a payload compound;

Z is absent or is R'N—, R'=H, alkyl, aryl or heteroaryl;

m is 0-40; and n is 1-20.

In an embodiment, G further comprises a triazole moiety.

In another aspect, provided herein is a pharmaceutical composition comprising the compound of formula (V) and a pharmaceutically acceptable carrier or excipient.

In another aspect, provided herein is a method of treating cancer in a patient, comprising administering to a patient in need thereof an effective amount of a compound of formula (V).

In another embodiment the labeling compound has the formula (VI):

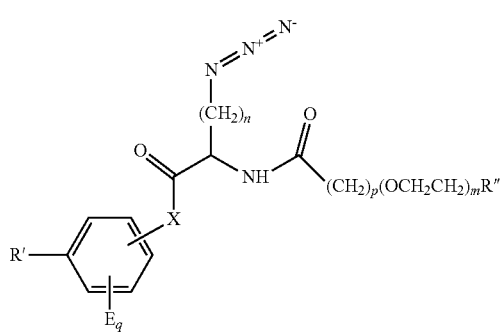

(VI)

wherein

E is a moiety selected from the group consisting of halogen, —CN, —NO$_2$, —SO$_2$, —SO$_2$NH$_2$, —S(O)$_2$C$_1$-C$_6$ alkyl, —S(O)$_2$aryl, —SO$_3$H and —OC$_1$-C$_6$ alkyl;

q is 0, 1, 2 3 or 4;

X=O, S, or Se;

m is 0-30, and n is 1-8, and p=1-8

R'''=OR''', SR''', (R'''=alkyl, aryl); FmocNH, t-BocNH; HCCH$_2$O; O=C—OR'''.

In another embodiment the labeling compound has the formula (VII):

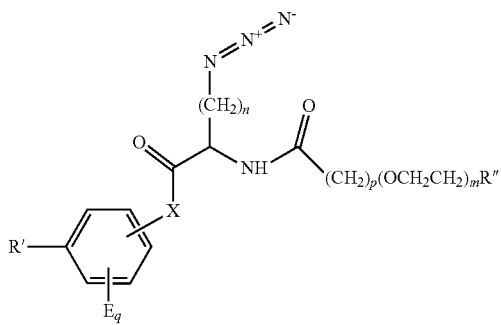

(VII)

E is a moiety selected from the group consisting of halogen, —CN, —NO$_2$, —SO$_2$, —SO$_2$NHW$^4$, —S(O)C$_1$-C$_6$ alkyl, —S(O)aryl, and —OC$_1$-C$_6$ alkyl;

X is O, S or Se; and

R' is —C(O)W$^1$, —SO$_2$W$^1$, —CH$_2$W$^2$, —C(O)W$^3$, —SO$_2$W$^3$, —C(O)W$^4$ or —SO$_2$W$^4$; wherein W$^1$ comprises a linear peptide of 1-25 amino acid residues, attached to C(O) or SO$_2$ at the N-terminus;

W$^2$ comprises a peptide of 1-25 amino acid residues, attached to CH$_2$ at an O-tyrosine or S-thiotyrosine residue;

W$^3$ comprises a peptide of 1-25 amino acid residues, attached to C(O) or SO$_2$ at the P-amino group of a 2,P-diamino-n-alkanoic acid residue, wherein P is 3, 4, 5, 6, 7 or 8;

W$^4$ comprises a peptide of up to 25 residues, linked to C(O) or SO$_2$ at the N-terminus;

q is 0, 1, 2 3 or 4.

Constructs Carrying Multiple Components

In embodiments, constructs carry two components (e.g., two drugs, two toxins, or one chelator and one toxin or two different drugs or two different toxins), that can be attached to an antibody site in a single simultaneous step. This facilitates combined targeted radioimmunotherapy and targeted therapy using antibody-drug conjugate (ADC) motifs, effectively doubling the size of the payload, e.g., toxins or drugs and results in conjugates that carry up to four or more therapeutically- or diagnostically-active entities per antibody. Labeling agents that carry two azide reactive handles, for example, are conveniently prepared via the sequence below to selectively label antibodies, converting them to ADCs with a DAR of 4.

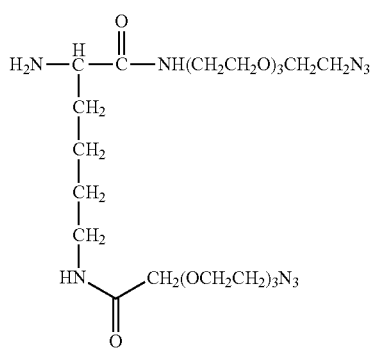

(1)

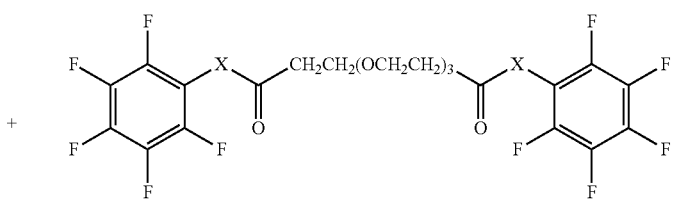

+

↓

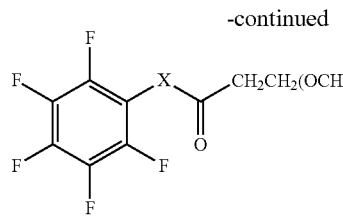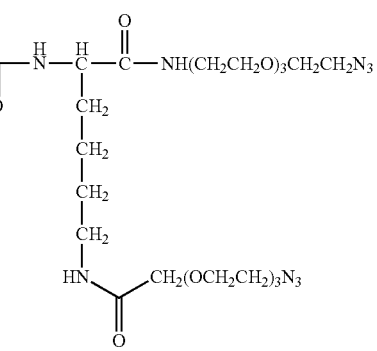

(2)

wherein X is either S or O.

In embodiments, the methods and compositions provided herein allow for selective labeling of antibodies with a drug-to antibody ratio (DAR) of 4. Using reagents of the type (2), four identical payloads on the antibody at the two antibody equivalent Lys 188 sites can be attached. In the scheme presented below, amines analogous to (1) can be used as precursors to agents analogous to (2) (not shown) that label antibodies at Lys 188 to give diverse types of multiple payloads.

In general antibodies to be modified are selected that result in efficient and selective site-specific labeling. A suitable target is provided by human kappa antibodies at a single lysine (Lys188) within the light-chain constant domain. In embodiments, certain residues are accorded their Kabat numbering; thus, $K^{188}$ CL kappa refers to residue 188 of the kappa light chain according to Kabat numbering, counting from the beginning of the kappa light chain. The artisan will appreciate that the numbering of the lysine residue may change depending on the specific numbering convention applied or because of alterations in the amino acid sequences that shorten or lengthen the polypeptide sequence.

Indeed, the bioorthogonal elements of these agents can be differentiated by standard synthetic routes (after Tsuchikama), which allows for placing different payloads on the target labeled antibody as shown schematically above.

Figure 11:
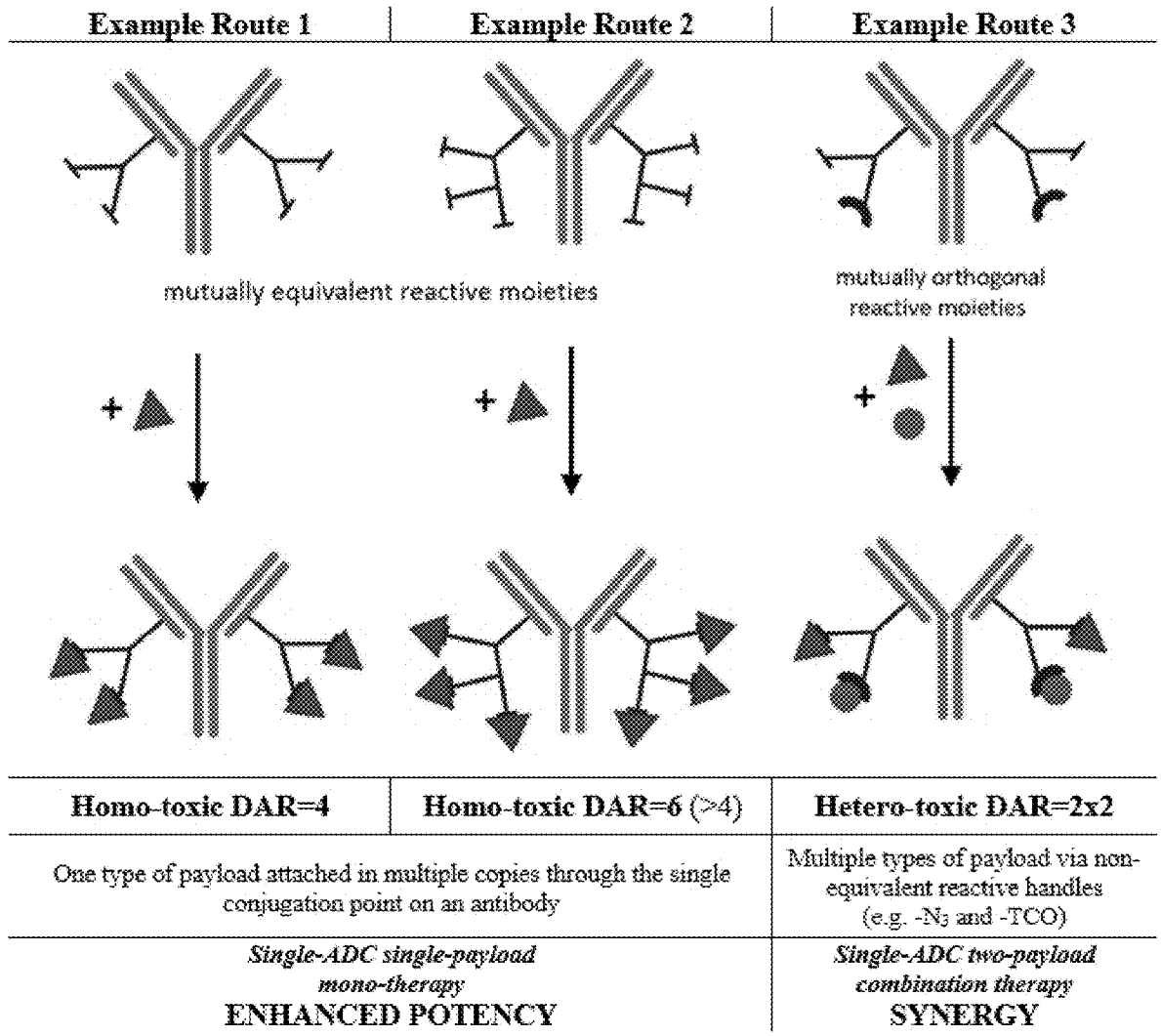
FIG. 11 shows example routes to obtain DAR4, DAR6, and DAR2×2 antibody conjugates.

It is important to emphasize that the ability to obtain an antibody conjugate, which carries multiple molecules of identical payload or more than one type of payload or drug on one molecule of antibody, but still requiring only one attachment point on the protein (FIG. 11), provides several very important advantages over the currently available non-site selective technologies. First, having a single and universal point of attachment (as the Lys-188 or its equivalent) on an antibody, allows to create an efficient, higher-capacity drug/payload delivery system with the smallest possible perturbation of the surface and overall structure of the antibody. Naturally, increasing drug/payload-to-antibody ratio without introducing the branching of the reactive handle (as in structure (2) and similar), requires to proportionally increase the number of attachment points on the antibody, dramatically increasing the risk of thermodynamically destabilizing the conjugate and lowering its affinity and thus selectivity towards the target epitope. This lowers effectiveness of the bioconjugate and translates into higher toxicities and lower therapeutic window. Second, because the conjugation methodology and structures presented herein (reagent (2) and alike) allow for attaching more than one type of a reactive handle to the single attachment point on each antibody light chain in a single chemical event, our disclosure provides a method to introduce two or more copies of two or more types of payloads onto each one of the two Lysine 188 residues (or its equivalents) in a single antibody molecule. This can be accomplished by using mutually orthogonally reactive handles doubled or even multiplied on the same branched acylating agent. Such an approach provides the ability to employ potential synergy between various pairs or larger groups of payloads when delivered simultaneously to the same target cell by the same delivery system. This way, for example, two cytotoxic payloads having different and non-competing mechanisms of action could be used to synergistically increase the selective toxicity of the conjugate, potentially widening the therapeutic window of the drug. A third critical advantage of such double-payload delivery systems would be a potential to address one of the most important deficiencies of the currently available antibody-drug conjugates used as anti-cancer drugs, namely, the widespread resistance to the toxic warheads carried by an ADC, which very often develops within the tumor. This is typically fueled by a high mutation rate of the cancer cells, which increases the heterogeneity of the tumor and its environment and consequently results in selection of the cancer cells resistant to the drug. Selecting for resistance is much less probable if two or more types of toxins (payloads), or a toxin and a DNA-damaging radionuclide are delivered simultaneously. This is because each cancer cell, in order to survive, needs to develop two independent resistance mechanisms at the same time, which is significantly less likely. Therefore, the branched antibody-drug conjugates carrying heterogenous and synergistic payloads in the form of the most stable conjugate with the least perturbed antibody surface, promise to dramatically improve their effectiveness as anti-cancer agents.

Chelate-Antibody Conjugates

Also provided are methods for site-selectively crosslinking chelators, e.g., radionuclide chelators, to antibodies and other proteins. This is accomplished through the agency of bifunctional chelators designed to label target proteins with bio-orthogonally reactive entities (ORE). In one embodiment, the preferred targets are the light chains of antibodies.

The present disclosure additionally provides practical, advanced methods for site-selective labeling of antibodies with radionuclide payloads through a stepwise process that includes first introducing a bioorthogonally reactive entity (e.g., azide) to the antibody surface, followed by reacting a corresponding bioorthogonally reactive partner (e.g., a DIBCO moiety) bearing a chelator, which can then be charged with an appropriate radionuclide The present disclosure further relates generally to the chemospecific union of antibodies with payloads, e.g., radionuclide payloads, via orthogonally reactive entities (ORE). In embodiments, the ORE have been attached site-selectively to the antibody surface using amine reactive entities such as phenolic esters or thioesters, in a specified manner or through the use of electrophiles linked to OREs.

The present disclosure also relates to the characterization and use of such compositions for diagnostic imaging purposes, or for the purpose of augmenting or modulating the activity of a radionuclide payload (e.g., biological molecule), or to introduce additional activities or payloads onto the antibody framework.

The present disclosure generally provides methods for the site-selective modification of monoclonal and polyclonal antibodies, their fragments (e.g., Fab, F(ab')$_2$, sdAb (single domain antibody)), bi-specific antibodies, diabodies), and the like. The modifications described herein can be used to attach payloads in radio-labeling for numerous diagnostic imaging and therapeutic antibody applications. The chelator compositions disclosed herein can be used for the treatment of many disorders, e.g., rheumatoid arthritis, bacterial and viral diseases, lupus erythematosus, psoriasis, multiple sclerosis, type-1 diabetes, Crohn's disease, and systemic sclerosis, Alzheimer disease, cancer, heart and liver disease (e.g., alcoholic liver disease), and cachexia.

The compositions disclosed herein can also be used in targeted therapeutics using chelators labeled with radionuclides ("targeted radionuclide therapy"). The use of antibodies that are covalently labeled to deliver therapeutics or toxins to target cells is well known as per antibody-drug conjugates. A similar approach involving the conjugation of antibodies to chelators with a high affinity for therapeutically viable radioisotopes has emerged. For example, there is high level interest in lutetium 177(177Lu) labeled pharmaceuticals as β-emitters (Banerjee S. et al., *Lutetium*-177 *therapeutic radiopharmaceuticals: linking chemistry, radiochemistry, and practical applications. Chem Rev.* 2015 Apr. 22; 115(8): 2934-74). As well, a strategy of targeted alpha-particle therapy (TAT) has emerged for soft-tissue metastases, (Scheinberg, D A and McDevit M R, *Actinium*-225 *in targeted alpha particle therapeutic applications, Curr Radiopharm.* 2011, 4, 306-320) whereby lethal α-emitting radionuclides are conjugated to tumor-targeting vectors using bifunctional chelators to selectively deliver cytotoxic alpha radiation to cancer cells. Actinium-225 (225Ac) is highly promising for use in TAT owing to its long 10-day half-life that is compatible with antibody-based targeting vectors and 4 high-energy α-emissions that are extremely lethal to cells.

A number of bifunctional chelators that can serve as a framework for targeted therapies have been developed. Such bifunctional chelators afford the option of connecting to antibodies, but the problem of product heterogeneity resulting from indiscriminant reactions of competing nucleophiles on the antibody surface has not been hereetofore addressed.

In an embodiment, site-selective covalent labeling of antibodies is performed using chelators of actinium and lutetium via a one or twostep mechanisms.

We have been able to achieve site-selective attachments of chelators to antibodies via a two-step process, which obviates a direct one step attack by systems that are likely to have a diverse and unpredictable range of reactivity. By optimizing the selectivity of a first step, which becomes the de facto determinant of the selectivity of the overall process, the outcome of payload conjugation can be assured and standardized. One can employ, in principle, a bioorthogonally reactive pair to accomplish this task, whereby a first "click-chemistry" partner can be selectively conjugated, and then linked quantitatively to a second complementary partner.

Indeed, an exemplary method features a first selective step that can be accomplished with an azido-linked-phenolate or thiophenolate that reacts primarily with Lys 188 of the conserved site of an antibody (FIG. 1). The azido group serves as a reactive handle that can be fused to DIBCO-functionalized payloads and represents a prototype that can be generalized for bioorthogonally reactive entities. For example, DIBCO-modified antibodies can also be combined with azido-functionalized payloads, as representative of the repertoire of click-chemistry motifs that can be deployed to forge stable linkages between antibodies and their target payloads. This repertoire includes tetrazine/(BCN) as described in Dommerholt J. et al., *Strain-Promoted* 1, 3-*Dipolar Cycloaddition of Cycloalkynes and Organic Azides., Top Curr Chem (Cham).* 2016 April; 374(2):16).

Figure 3:
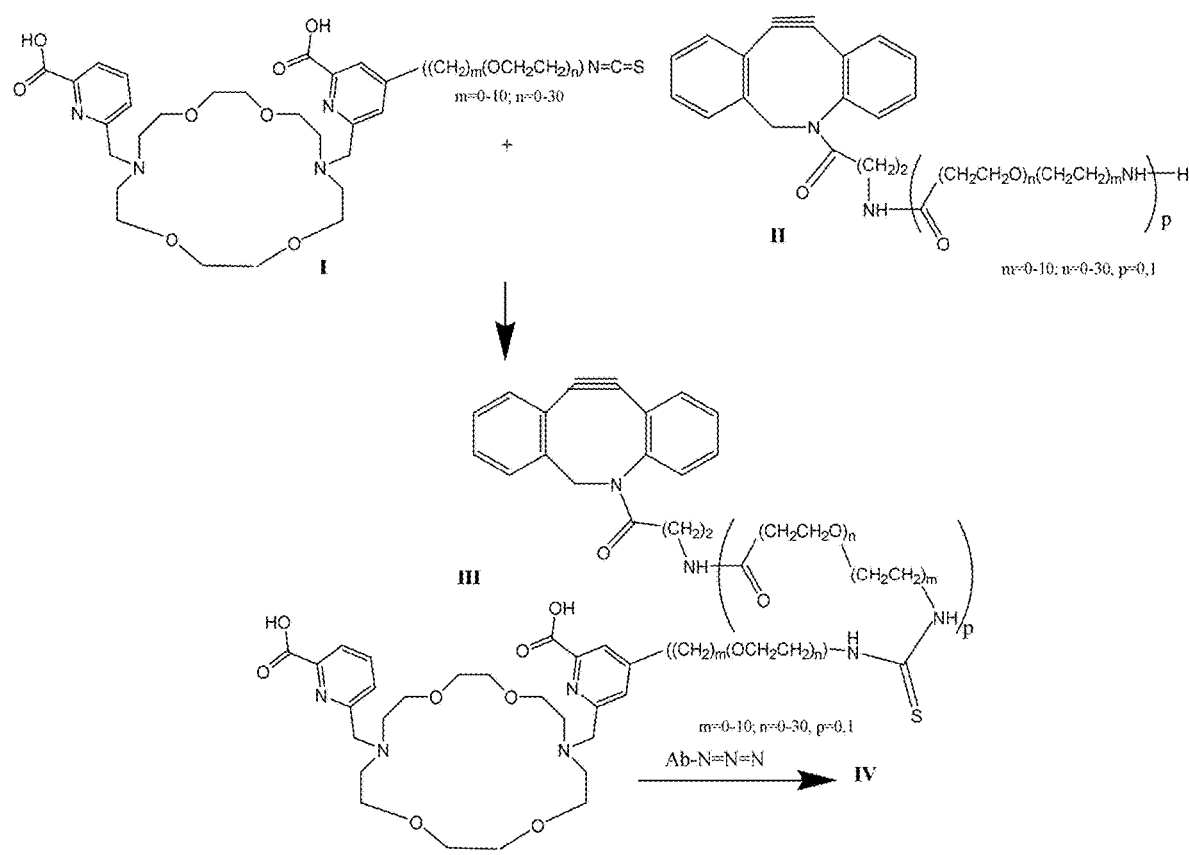
FIG. 3 depicts in structures I-IV a general scheme for conjugation of Macropa to antibodies employing the $H_2$macropa-NCS and various DIBCO-amines to generate the thiourea precursor for linkage to an azido-labeled antibody.
Figure 4:
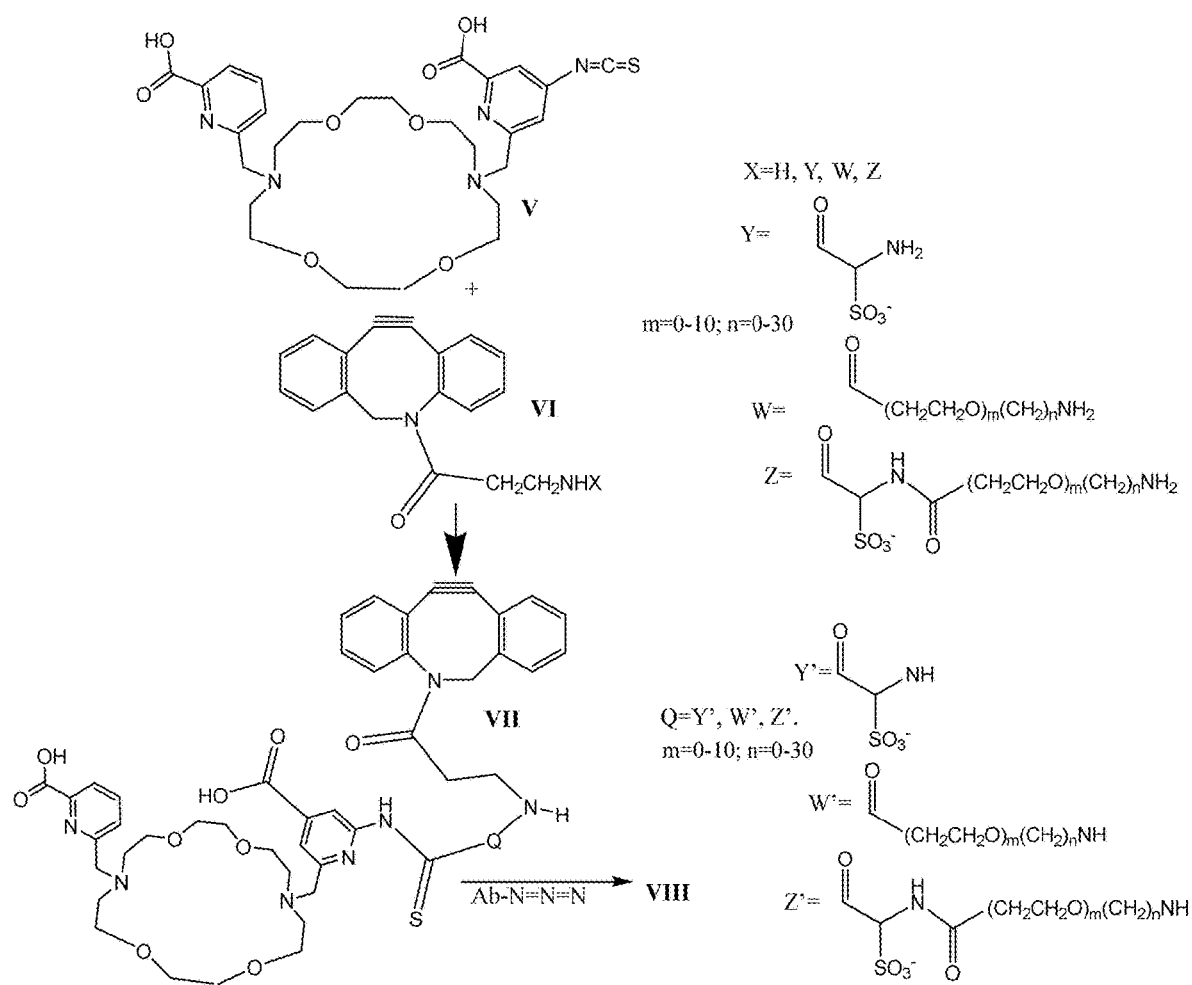
FIG. 4 depicts in structures V-VIII the reaction of various DIBCO amines with $H_2$macropa-NCS as a route to DIBCO-thiourea entities for condensation with azido-labeled antibodies.
Figure 5:
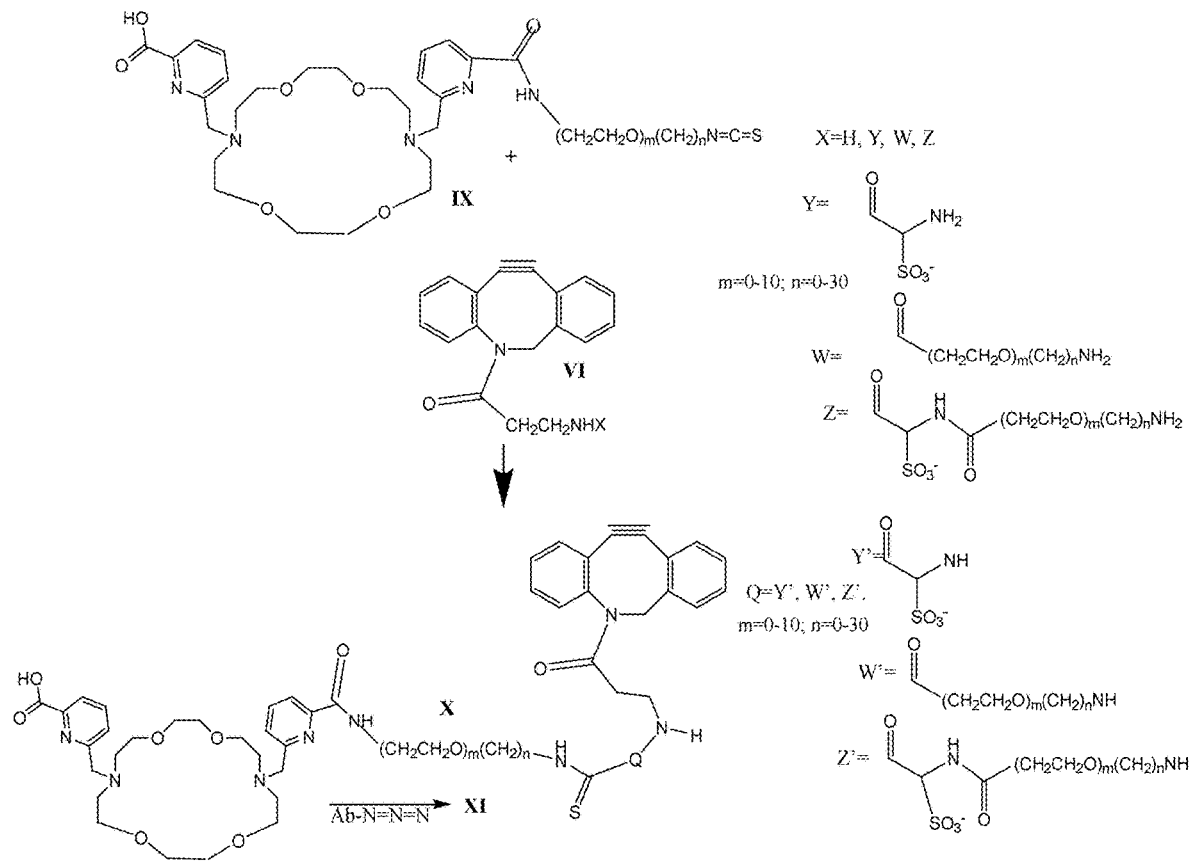
FIG. 5 depicts in structures VI and IX-XI the reaction of various DIBCO amines with $H_2$macropa-derived isothiocyanates as a route to DIBCO-thiourea entities for condensation with azido-labeled antibodies.
Figure 6:
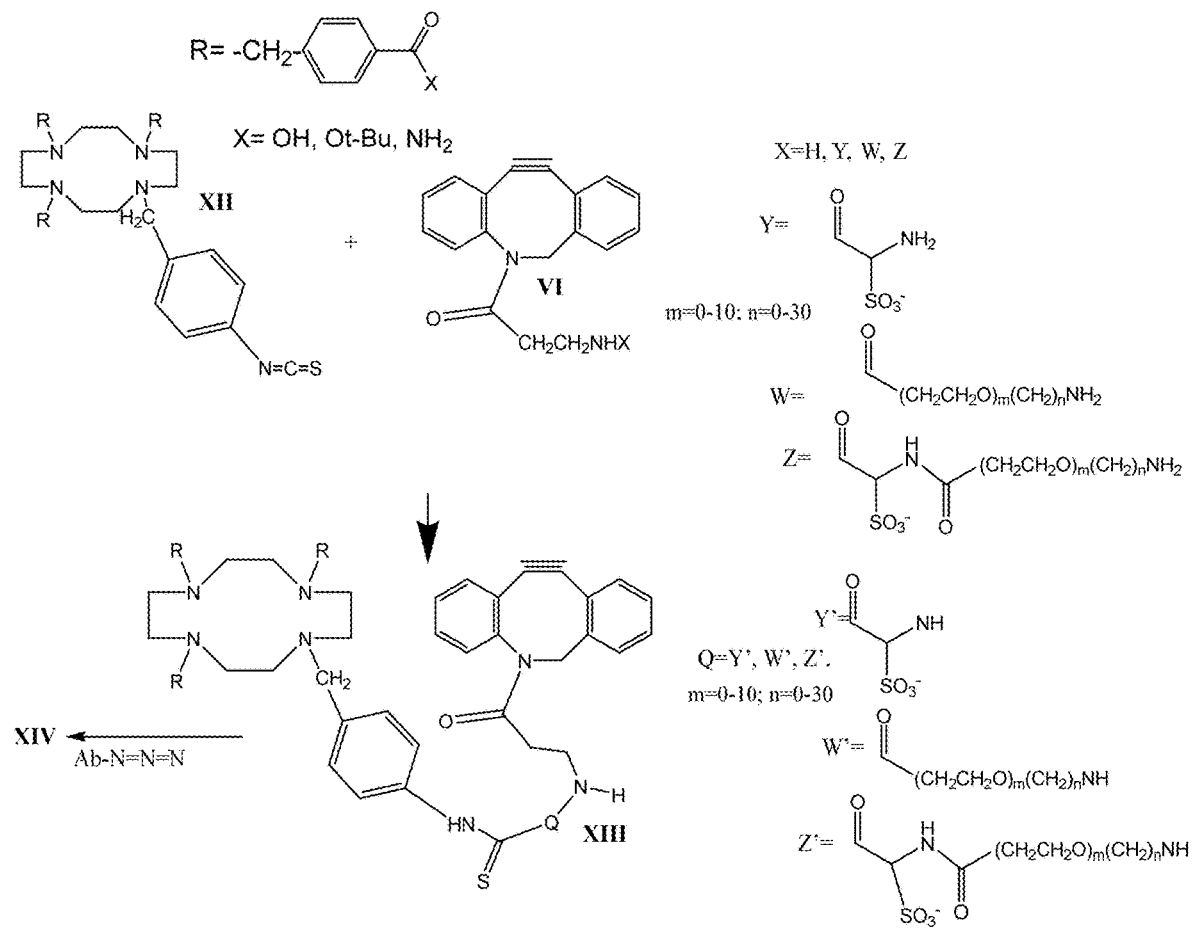
FIG. 6 depicts in structures VI, XII, XIII, and XIV the reaction of various DIBCO amines with DOTA-isothiocyanates as a route to DIBCO-thiourea entities for condensation with azido-labeled antibodies.
Figure 7:
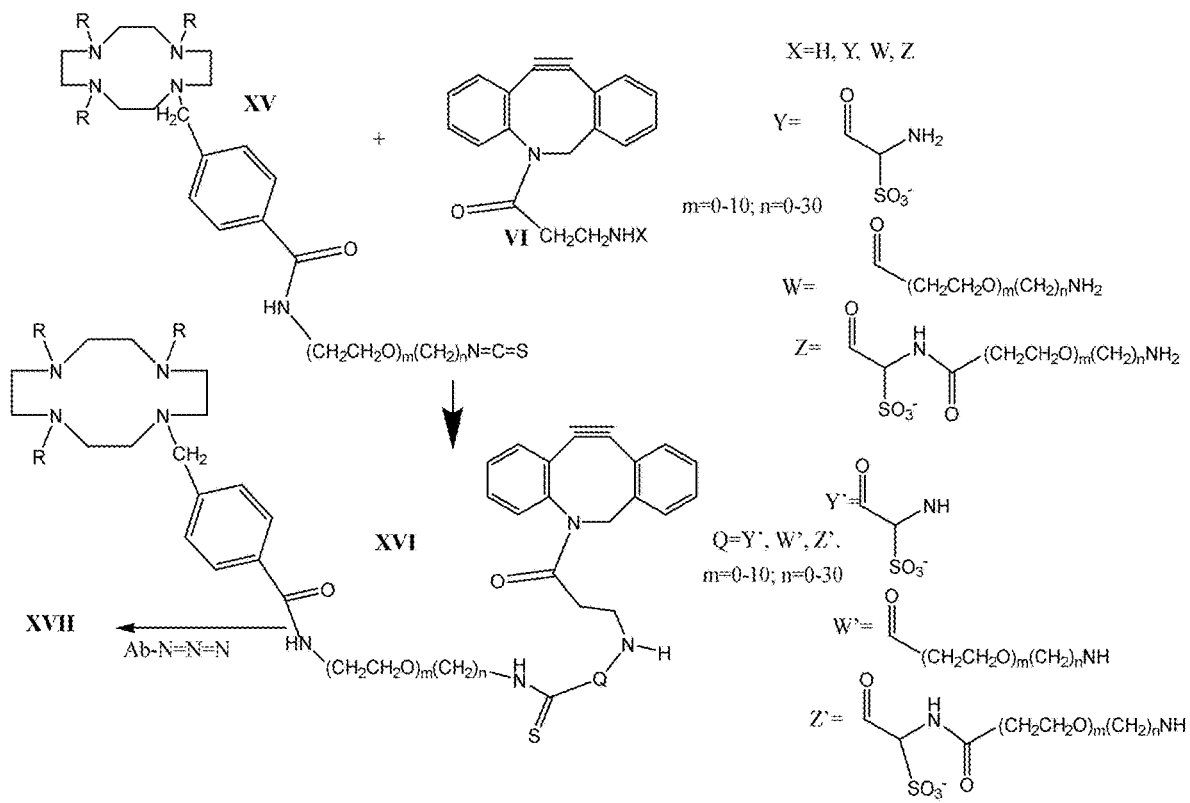
FIG. 7 depicts in structures VI, XV, XVI, and XVII the reaction of various DIBCO amines with a DOTA-NHS ester as a route to DIBCO-thiourea entities for condensation with azido-labeled antibodies.
Figure 8:
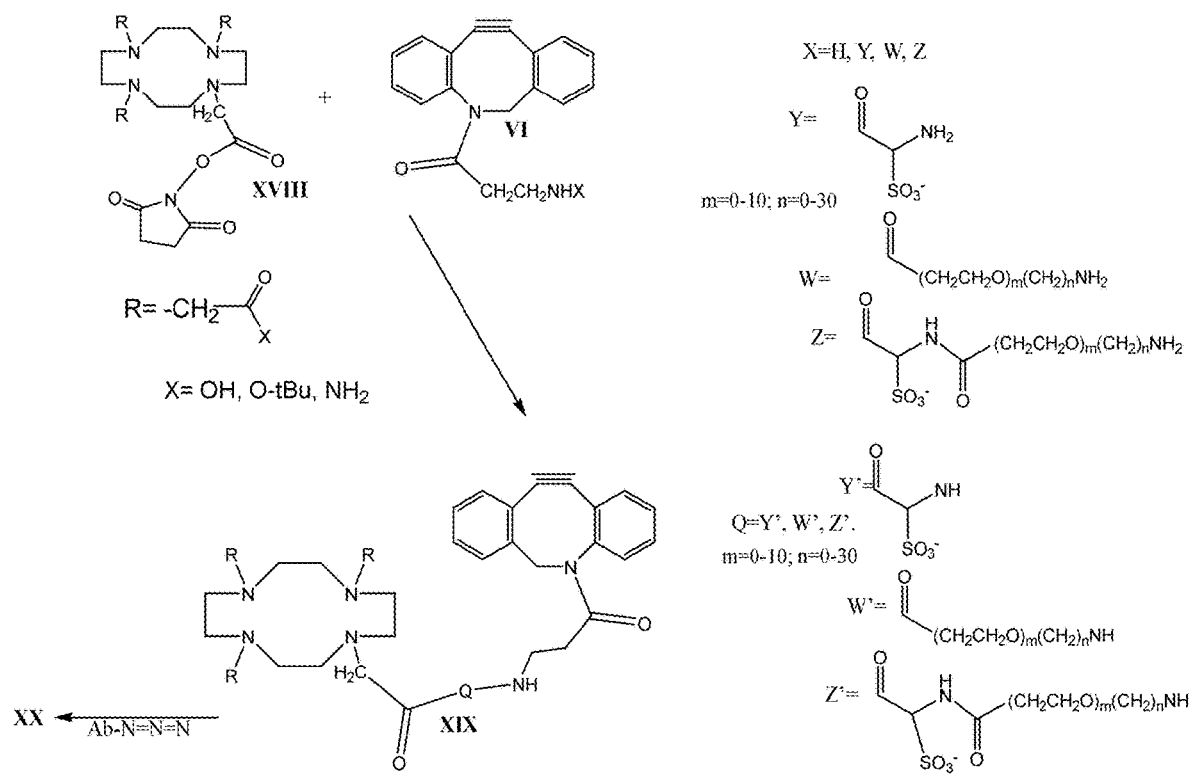
FIG. 8 depicts in structures VI, XVIII, XIX, and XX the reaction of various DIBCO amines with various DOTA-isothiocyanates as a route to DIBCO-thiourea entities for condensation with azido-labeled antibodies.
Figure 9:
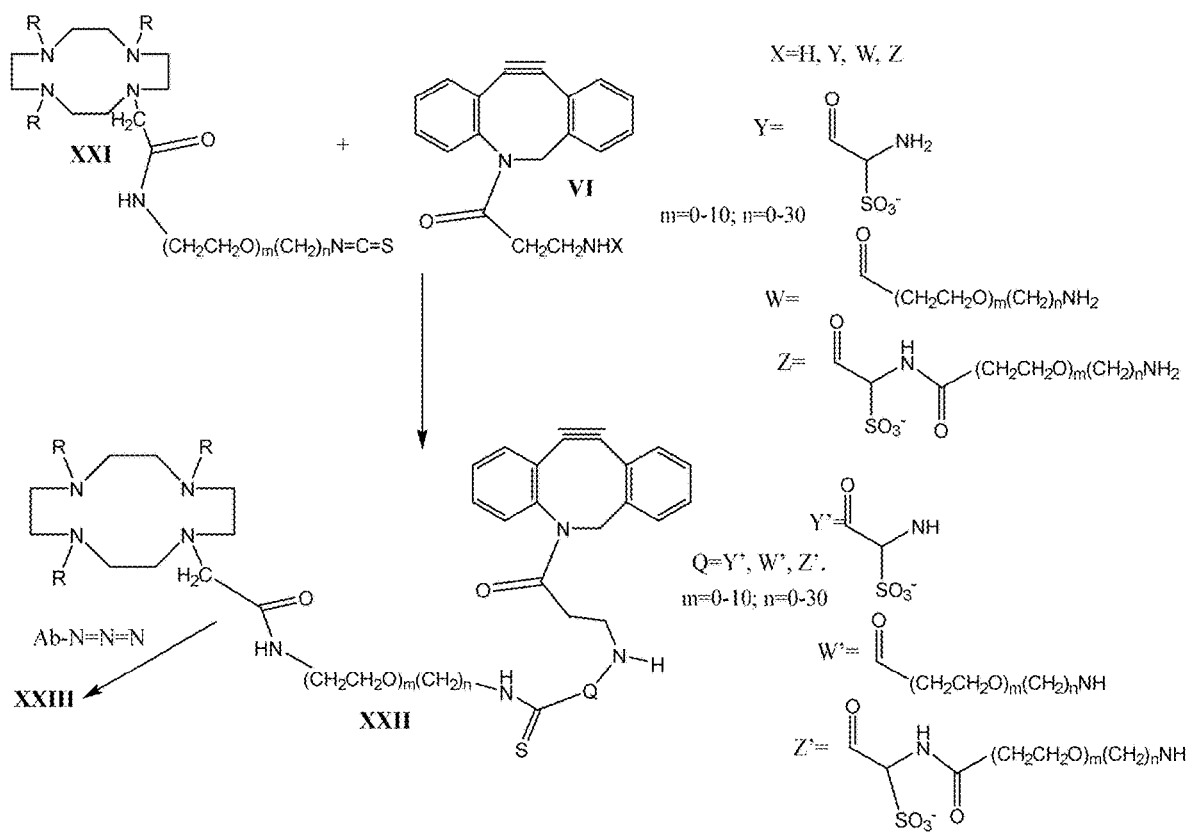
FIG. 9 depicts in structures VI, XXI, XXII, and XXIII the reaction of various DOTA-isothiocyanates as a route to DIBCO-thiourea entities for condensation with azido-labeled antibodies.

In this context, the kinetic and thermodynamic properties of actinium chelation with H$_2$macropa afford opportunities to prepare actinium chelates, site-selectively linked to therapeutic antibodies (Thiele N A et al., *An Eighteen-Membered Macrocyclic Ligand for Actinium*-225 *Targeted Alpha Therapy. Angew Chem Int Ed Engl.* 2017 Nov. 13; 56(46): 14712-14717). The antibody can be linked to the H$_2$macropa entity through a general sequence depicted in FIG. 3 in which various DIBCO amines II are first condensed with H$_2$macropa isothiocyanates I, and the resulting DIBCO-thiourea III is condensed with the azido-labeled antibody Ab-N=N=N to give a chelator-antibody adduct. The latter is then treated with actinium to produce the desired site-selectively conjugated radio-labeled material. FIGS. 3-5 exemplify embodiments in which antibodies bearing actinium chelators can be produced site-selectively, by exploiting the site-selective conjugation of the azide-bearing entity.

Analogous sequences (FIGS. 6-9) can be employed with DOTA isothiocyanates to provide DIBCO-linked DOTA chelators that can be conjugated to various azide-linked antibodies that have been site-selectively modified at Lys-188.

Figure 10:
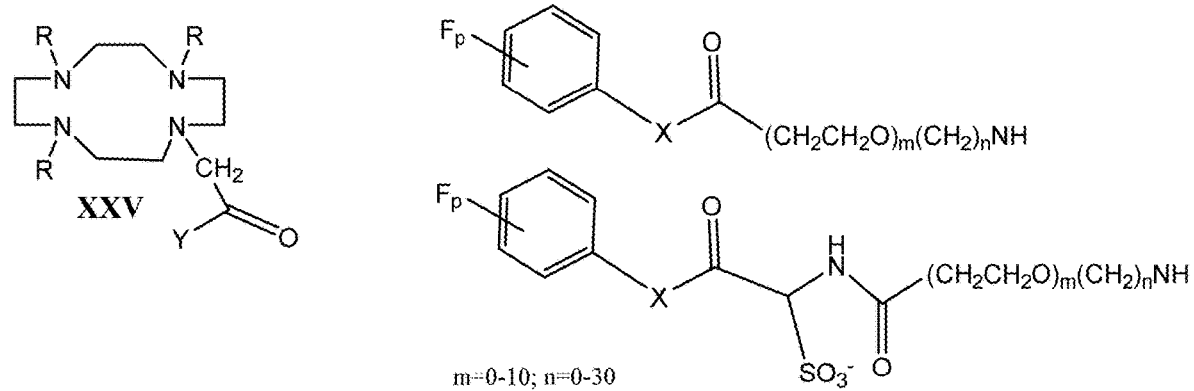
FIG. 10 shows phenolic and thiophenolic esters for selective conjugation of DOTA-chelators to $IgG_1$ antibodies.

Alternatively, certain ADCs corresponding to formulas XXIV and XXV (see FIG. 10) that are comprised of conjugates bearing chelators can also be selectively linked to antibodies through microbial transglutaminase-mediated exchange. This sequence can be used to provide chelators with a CAR=2, or combined with the aforementioned acylation reactions to give a CAR=4. A CAR=4 can also be achieved by adapting branched linkers (Anami Y. et al., *Enzymatic conjugation using branched linkers for constructing homogeneous antibody-drug conjugates with high potency. Org Biomol Chem.* 2017 Jul. 5; 15(26): 5635-5642) to routes described above to antibody-linked chelators.

Methods

Provided herein are methods of treating a disease or condition known or suspected to benefit from treatment with a composition according to the disclosure.

The subject considered herein is typically a human. However, the subject can be any mammal for which treatment is desired. Thus, the methods described herein can be applied to both human and veterinary applications.

Administration/Dose

The formulation of therapeutic compositions and their subsequent administration (dosing) is within the skill of those in the art. Dosing is dependent on severity and responsiveness of the disease state to be treated, with the course of treatment lasting from several days to several months, or until a sufficient diminution of the disease state is achieved. Optimal dosing schedules can be calculated from measurements of drug accumulation in the body of the patient.

Persons of ordinary skill can easily determine optimum dosages, dosing methodologies and repetition rates. Optimum dosages may vary depending on the relative potency of individual compositions according to the disclosure, and can generally be estimated based on $EC_{50}$s found to be effective in in vitro and in vivo animal models. In general, dosage is from 0.01 μg to 100 g/kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the composition according to the disclosure is administered in maintenance doses, ranging from 0.01 μg to 100 g/kg of body weight, once or more daily, to once every 20 years.

In some embodiments, the pharmaceutical composition is administered alone.

In some embodiments, the pharmaceutical composition is administered in a therapeutically effective amount or dosage. A "therapeutically effective amount" is an amount that, when administered to a patient by itself, effectively treats a muscle disease, a viral infection, or a bacterial infection. An amount that proves to be a "therapeutically effective amount" in a given instance, for a particular subject, may not be effective for 100% of subjects similarly treated for the disease or condition under consideration, even though such dosage is deemed a "therapeutically effective amount" by skilled practitioners.

In different embodiments, the composition can modulate the expression of a gene involved in a muscle disease, a viral infection, or a bacterial infection.

While the amounts should result in the effective treatment of a muscle disease, a viral infection, or a bacterial infection, the amounts, are preferably not excessively toxic to the patient (i.e., the amounts are preferably within toxicity limits as established by medical guidelines). In some embodiments, either to prevent excessive toxicity or provide a more efficacious treatment, or both, of a muscle disease, a viral infection, or a bacterial infection, a limitation on the total administered dosage is provided. Typically, the amounts considered herein are per day; however, half-day and two-day or three-day cycles also are considered herein.

Different dosage regimens may be used to treat a muscle disease, a viral infection, or a bacterial infection. In some embodiments, a daily dosage, such as any of the exemplary dosages described above, is administered once, twice, three times, or four times a day for three, four, five, six, seven, eight, nine, or ten days. Depending on the stage and severity of the disease being treated, a shorter treatment time (e.g., up to five days) may be employed along with a high dosage, or a longer treatment time (e.g., ten or more days, or weeks, or a month, or longer) may be employed along with a low dosage. In some embodiments, a once- or twice-daily dosage is administered every other day.

Pharmaceutical compositions with compounds of the disclosures or their pharmaceutically acceptable salts or solvate forms, in pure form or in an appropriate pharmaceutical composition, can be administered via any of the accepted modes of administration or agents known in the art. The compounds can be administered, for example, orally, nasally, parenterally (intravenous, intramuscular, or subcutaneous), topically, transdermally, intravaginally, intravesically, intracisternally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, for example, in unit dosage forms suitable for simple administration of precise dosages. A particular route of administration is oral, particularly one in which a convenient daily dosage regimen can be adjusted according to the degree of severity of the disease to be treated.

Auxiliary and adjuvant agents may include, for example, preserving, wetting, suspending, sweetening, flavoring, perfuming, emulsifying, and dispensing agents. Prevention of the action of microorganisms is generally provided by various antibacterial and antifungal agents, such as, parabens, chlorobutanol, phenol, sorbic acid, and the like. Isotonic agents, such as sugars, sodium chloride, and the like, may also be included. Prolonged absorption of an injectable pharmaceutical form can be brought about by the use of agents delaying absorption, for example, aluminum monostearate and gelatin. The auxiliary agents also can include wetting agents, emulsifying agents, pH buffering agents, and antioxidants, such as, for example, citric acid, sorbitan monolaurate, triethanolamine oleate, butylated hydroxytoluene, and the like.

Solid dosage forms can be prepared with coatings and shells, such as enteric coatings and others well-known in the art. For example, they can contain pacifying agents and can be of such composition that they release the active compounds in a certain part of the intestinal tract in a delayed manner. Examples of embedded compositions that can be used are polymeric substances and waxes. The active agents according to the disclosure also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the conjugates described herein, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethyl formamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Generally, depending on the intended mode of administration, the pharmaceutically acceptable compositions will contain about 1% to about 99% by weight of the compositions described herein, or a pharmaceutically acceptable salt thereof, and 99% to 1% by weight of a pharmaceutically acceptable excipient. In one example, the composition will be between about 5% and about 75% by weight of a composition described herein, or a pharmaceutically acceptable salt thereof, with the rest being suitable pharmaceutical excipients.

Actual methods of preparing such dosage forms are known, or will be apparent, to those skilled in this art. Reference is made, for example, to Remington's Pharmaceutical Sciences, 18th Ed. (Mack Publishing Company, Easton, Pa., 1990).

Kits

In other embodiments, kits are provided. Kits typically include package(s) comprising compositions according to the disclosure.

The phrase "package" means any vessel containing presented herein. In some embodiments, the package can be a box or wrapping. Packaging materials for use in packaging pharmaceutical products are well-known to those of skill in the art. Examples of pharmaceutical packaging materials include, but are not limited to, bottles, tubes, inhalers, pumps, bags, vials, containers, syringes, bottles, and any packaging material suitable for a selected formulation and intended mode of administration and treatment.

The kit can also contain items that are not contained within the package, but are attached to the outside of the package, for example, pipettes.

EXAMPLES

Examples have been set forth below for the purpose of illustration and to describe certain specific embodiments of the disclosure. However, the scope of the claims is not to be in any way limited by the examples set forth herein. Various changes and modifications to the disclosed embodiments will be apparent to those skilled in the art and such changes and modifications including, without limitation, those relating to the chemical structures, substituents, derivatives, formulations or methods of the disclosure may be made without departing from the spirit of the disclosure and the scope of the appended claims. Definitions of the variables in the structures in the schemes herein are commensurate with those of corresponding positions in the formulae presented herein.

Example 1: Ester Synthesis Protocols

Esters used in the compositions and methods described herein were prepared as follows:

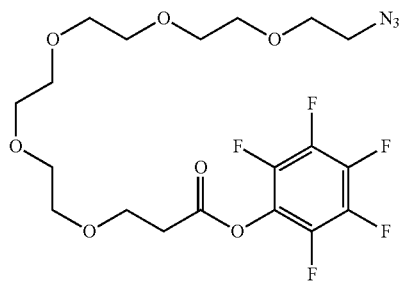

Azido-PEG$_5$-(CH$_2$)$_2$-pentafluorophenol ester

N$_3$-PEG$_5$-(CH$_2$)$_2$—COOH 22 mg (65 uM), HBTU 25 mg (65 uM) and N,N-diisopropylethylamine 23 uL (132 uM) were dissolved in DMF (0.5 mL) and shaken for 30 sec.

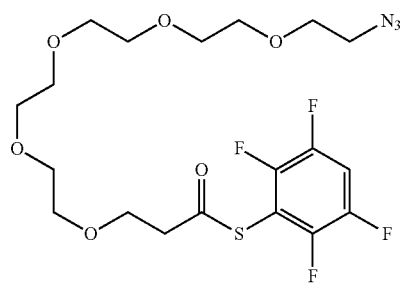

Azido-PEG$_5$-(CH$_2$)$_2$-2,3,5,6-tetrafluorothiophenol ester

To the resulting solution pentafluorophenol 6 mg (42 uM) was added and allowed to stir for 1 hr at RT. The crude mixture was purified by RP-HPLC.

N$_3$-PEG$_5$-(CH$_2$)$_2$—COOH 30 mg (89 uM), pyBOP 44 mg (85 uM) and N,N-diisopropylethylamine 30 uL (173 uM) were dissolved in DMF (0.5 mL) and shaken for 30 sec. To the resulting solution 2,3,5,6-tetrathiophenol 7.6 mg (42 uM) was added and allowed to stir for 1 hr at RT. The crude mixture was purified by RP-HPLC.

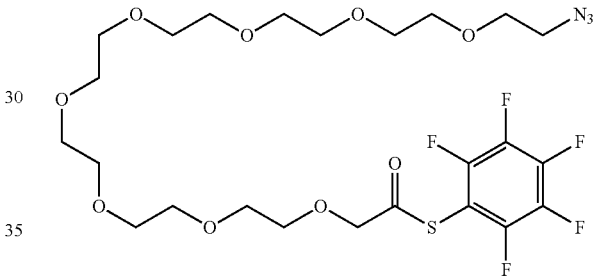

Azido-PEG$_8$-CH$_2$-pentafluorothiophenol ester

Pentafluorothiophenol 20 mg (100 uM) and N$_3$-PEG$_8$-CH$_2$—COOH 45 mg (100 uM) were dissolved in DCM (1 mL) and cooled to 0° C. To the resulting solution DCC 25 mg (120 uM) and DMAP 36 uL (10 mg/mL) were added and allowed to stir at 0° C. to RT for 16 hrs. The generated DCU was removed by filtration and the filtrate was concentrated, dissolved in acetonitrile/water and purified by RP-HPLC.

Conjugation of the Bio-Orthogonal Reactive Handles to Antibodies

Modification protocols using several acylating reagents claimed herein as used for three different recombinant antibodies (Trastuzumab, Palivizumab and Antibody #247) are presented here to exemplify the highly site-selective character of the conjugation of various bio-orthogonal handles under the reagent-optimized conditions.

1. Acylation of an antibody P was carried out by adding a solution of the protein in PBS buffer pH 7.4 to a solution of the modifying reagent R prepared in anhydrous, amine-free N,N-dimethylformamide to reach the final concentration of the protein of X μM and a molar excess of the modifying reagent over the protein of Y times.
2. The acylation reaction was allowed to proceed for T minutes at the temperature of Z (room temp, or on ice) as summarized in the Table below.
3. For the purpose of the second-step conjugation (click reaction), the first conjugation reagent (acylation reagent) was either: a) removed by size exclusion chromatography on a Zeba Spin™ column or by ultrafiltration or b) quenched by lowering pH to 5.6, or addition of approx. 10-100× excess of hydroxylamine (pH 7.4) or gamma-aminobutyric acid (pH 7.4), and subsequently removed by a size exclusion chromatography on a Zeba Spin™ column or by ultrafiltration.

Compounds A through N show representative Electrospray Ionization (ESI) LC-Mass Spectrometric analyses of antibodies modified according to the described protocol. Table 1 below lists the experimental parameters for each acylation reaction. All ESI-MS analyses were performed on antibody samples reduced with Tris(2-carboxyethyl) phosphine hydrochloride (TCEP) and routine RP LC-MS analyses were employed.

Table 1: shows various proteins and their corresponding conjugation reagents.

| Comp. | Protein P | Conjugation Reagent R | Prot. [uM] X | Acryl. Excess Y | Time [min] T | Temp Z |
|---|---|---|---|---|---|---|
| A. | Trastuzumab | 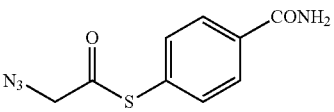 [SMILES: [N-]=[N+]=NCC(=O)Sc1ccc(C(N)=O)cc1] | 2 | 16 | 15 | RT |
| B. | Trastuzumab | 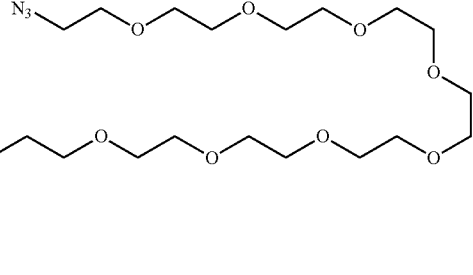 | 2 | 24 | 115 | RT |
| C. | Trastuzumab | 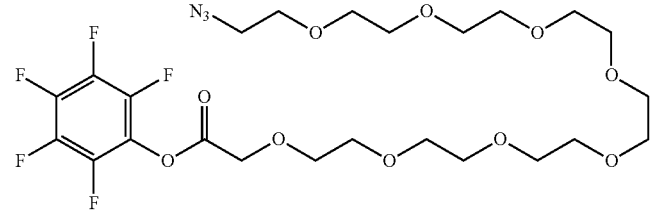 [SMILES: [N-]=[N+]=NCCOCCOCCOCCOCCOCCOCCOCCOCC(=O)Oc1c(F)c(F)c(F)c(F)c1F] | 2 | 16 | 75 | RT |
| D. | Trastuzumab | 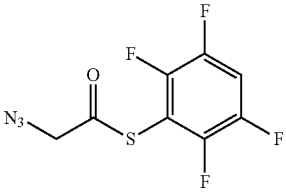 [SMILES: [N-]=[N+]=NCC(=O)Sc1c(F)c(F)cc(F)c1F] | 2 | 8 | 15 | RT |
| E. | Trastuzumab | | 2 | 5 | 15 | RT |
| F. | Trastuzumab | 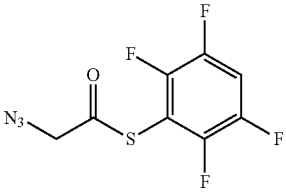 [SMILES: [N-]=[N+]=NCC(=O)Sc1c(F)c(F)cc(F)c1F] | 2 | 8 16 | 15 | RT |
| G. | Trastuzumab | 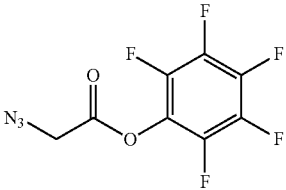 [SMILES: [N-]=[N+]=NCC(=O)Oc1c(F)c(F)c(F)c(F)c1F] | 2 | 16 | 75 | RT |
| H. | Palivizumab | | 2 | 16 | 75 | RT |
| I. | Ab#247 | | 2 | 16 | 75 | RT |
| J. | Trastuzumab | | 10 | 8 | 120 | 0° C. |

-continued

| Comp. | Protein P | Conjugation Reagent R | Prot. [uM] X | Acryl. Excess Y | Time [min] T | Temp Z |
|---|---|---|---|---|---|---|
| K. | Trastuzumab | 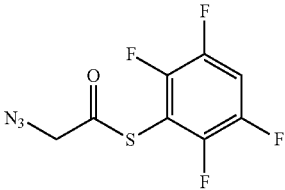 | 2 | dosing | 6 × 10 | 0° C. |
| L. | Trastuzumab | 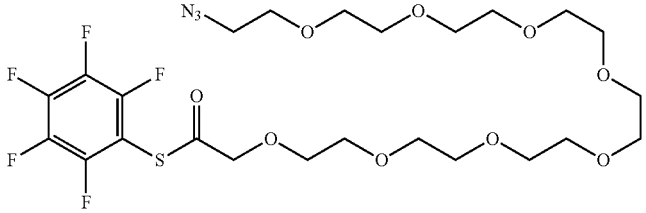 [SMILES: [N-]=[N+]=NCCOCCOCCOCCOCCOCCOCCOCCOCC(=O)Oc1c(F)c(F)c(F)c(F)c1F] | 2 | 20 | 120 | 0° C. |
| M. | Trastuzumab | 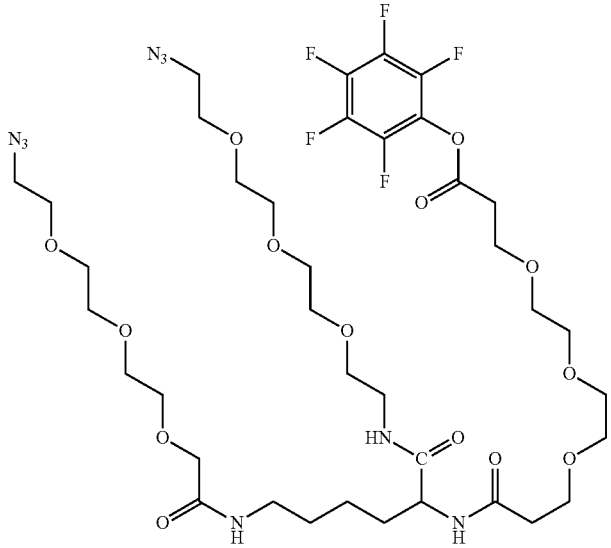 [SMILES: [N-]=[N+]=NCCOCCOCCOCCNC(=O)C(CCCCNC(=O)COCCOCCOCCN=[N+]=[N-])NC(=O)CCOCCOCCOCCC(=O)Oc1c(F)c(F)c(F)c(F)c1F] | 10 | 60 | 135 | 0° C. |
| N. | Palivizumab | | 10 | 60 | 135 | 0° C. |

Compound A. Site-selective modification of Trastuzumab using Azidoacetyl-4-mercaptobenzamide. Modification conditions are further described in Table 1 The resulting azido-Trastuzumab was analyzed by ESI-MS. M/z shift for the modified species is approx. +83 Da.

Compound B. Site-selective modification of Trastuzumab using Azido-PEG$_8$-CH$_2$CH$_2$-Pentafluorophenyl ester. Modification conditions are further described in Table 1 The resulting azido-Trastuzumab was further reacted with >20-fold excess of dibenzoazacyclooctyne-CO—CH$_2$CH$_2$-amine and subsequently analyzed by ESI-MS. M/z shift for the modified species is approx. +725 Da.

Compound C. Site-selective modification of Trastuzumab using Azido-PEG$_8$-CH$_2$-Pentafluorophenyl ester and efficient click-reaction with a DIBAC-derivative of the desired payload. Modification conditions are further described in Table 1. The resulting azido-Trastuzumab was further reacted with ~20-fold excess of dibenzoazacyclooctyne-derivative of a mushroom toxin, alpha-amanitin, and subsequently analyzed by ESI-MS. M/z shift for the modified species is approx. +435 Da and +1916 Da for azido-trastuzumab and the final product of the click reaction, respectively.

Compound D. Site-selective modification of Trastuzumab using Azido-acetyl-Tetrafluorothiophenyl ester. Modification conditions are further described in Table 1. The resulting azido-Trastuzumab was analyzed by ESI-MS. M/z shift for the modified species is approx. +83 Da.

Compound E. Site-selective modification of Trastuzumab using Azido-acetyl-Tetrafluorothiophenyl ester. Modification conditions are further described in Table 1 The resulting azido-Trastuzumab was further reacted with >20-fold excess of dibenzoazacyclooctyne-CO—CH$_2$CH$_2$-amine and subsequently analyzed by ESI-MS. M/z shift for the modified species is approx. +360 Da.

Compound F. Site-selective modification of Trastuzumab using Azido-acetyl-Pentafluorophenyl ester. Modification conditions are further described in Table 1. The resulting azido-Trastuzumab was analyzed by ESI-MS. M/z shift for the modified species is approx. +83 Da.

Compound G. Site-selective modification of Trastuzumab using Azido-PEG$_8$-CH$_2$-Pentafluorophenyl ester. Modification conditions are further described in Table 1. The resulting azido-Trastuzumab was further reacted with >20-fold excess of dibenzoazacyclooctyne-CO—CH$_2$CH$_2$-amine and subsequently analyzed by ESI-MS. M/z shift for the modified species is approx. +712 Da.

Compound H. Site-selective modification of Palivizumab using Azido-$PEG_8$-$CH_2$-Pentafluorophenyl ester and efficient click-reaction with a DIBAC-derivative of the desired payload. Modification conditions are further described in Table 1 The resulting azido-Palivizumab was further reacted with ~20-fold excess of dibenzoazacyclooctyne-derivative of a mushroom toxin, alpha-amanitin, and subsequently analyzed by ESI-MS. M/z shift for the modified species is approx. +1916 Da for the final product of the click reaction.

Compound I. Site-selective modification of Antibody #247 using Azido-$PEG_8$-$CH_2$-Pentallùorophenyl ester and efficient click-reaction with a DIBAC-derivative of the desired payload. Modification conditions are further described in Table 1. The resulting azido-Antibody#247 was further reacted with ~20-fold excess of dibenzoazacyclooctyne-derivative of a mushroom toxin, alpha-amanitin, and subsequently analyzed by ESI-MS. M/z shift for the modified species is approx. +1916 Da for the final product of the click reaction.

Compound J. Site-selective modification of Trastuzumab on ice, and at a higher protein concentration of 10 uM, using Azido-$PEG_8$-$CH_2$-Pentafluorophenyl ester. Modification conditions are further described in Table 1. The resulting azido-Trastuzumab was analyzed by ESI-MS. M/z shift for the modified species is approx. +436 Da.

Compound K. Site-selective modification of Trastuzumab on ice using 6 consecutive, equal doses (~6.7 total molar excess over IgG) of Azido-acetyl-Tetrafluorothiophenyl ester. Total contact time was ~1h. Modification conditions are further described in Table 1. The resulting azido-Trastuzumab was further reacted with >20-fold excess of dibenzoazacyclooctyne-CO—$CH_2CH_2$-amine and subsequently analyzed by ESI-MS. M/z shift for the modified species is approx. +360 Da.

Compound L. Site-selective modification of Trastuzumab on ice using Azido-$PEG_8$-$CH_2$-Pentafluorothiophenyl ester. Modification conditions are further described in Table 1. The resulting azido-Trastuzumab was further reacted with >20-fold excess of dibenzoazacyclooctyne-CO—$CH_2CH_2$-amine and subsequently analyzed by ESI-MS. M/z shift for the modified species is approx. +712 Da.

Compound M. Site-selective modification of Trastuzumab on ice, and at a higher protein concentration of 10 uM, using a branched Bis-(Azido-$PEG_3$)-Lysyl-$PEG_3$-$CH_2CH_2$-Pentafluorophenyl ester. Modification conditions are further described in Table 1. The resulting azido-Trastuzumab was analyzed by ESI-MS. M/z shift for the modified species is approx. +776 Da.

Compound N. Site-selective modification of Palivizumab on ice, and at a higher protein concentration of 10 uM, using a branched Bis-(Azido-$PEG_3$)-Lysyl-$PEG_3$-$CH_2CH_2$-Pentafluorophenyl ester. Modification conditions are further described in Table 1The resulting azido-Palivizumab was analyzed by ESI-MS. M/z shift for the modified species is approx. +776 Da.

Confirmation of the Biological Efficacy of the Antibody-Payload Conjugates

Several antibody-drug conjugates were prepared in a scale suitable for functional analyses in order to provide evidence that their biological activity (e.g. binding to their target epitope on cancer cells) and therapeutic potential are preserved. In one of the tests, Trastuzumab was site-selectively conjugated to one of the two different chelating agents of interest (DIBAC-PEG4-thiourea-MacroPa and DIBAC-DO3A, see FIG. 2),

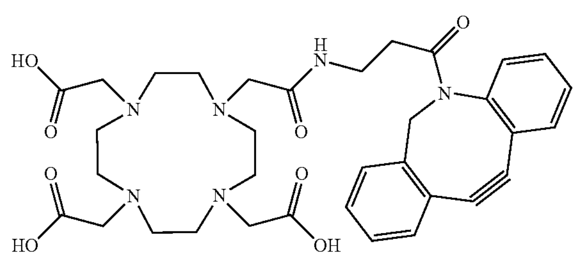

DIBAC-DO3A

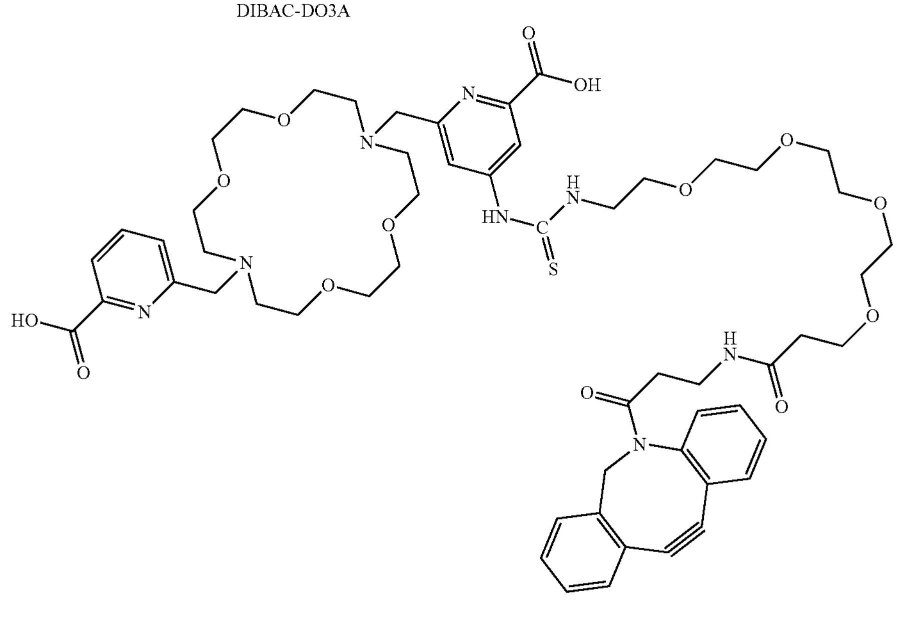

DIBAC-PEG4-thiourea-MacroPa using our protocol developed for the acylating agent Azido-PEG$_8$-CH$_2$-pentafluorophenolate, and both were tested for their binding to HER-2 positive cancer cell lines (OVCAR and JIMT-1) using a standard Fluorescence-Activated Cel Sorting (FACS) analysis. This analysis showed that the apparent dissociation constants (Kd) for both of the conjugates were practically indistinguishable from the naked (unmodified) Trastuzumab, used as a positive control for binding. Similarly, other conjugate of Trastzumab, carrying a DIBAC-Toxin of choice (a conjugate prepared using reagent A in table above and carrying a variant of DIBAC-Amanitin) exhibited binding to NCI-N87, SKBR-3 and JIMT-1 cancer cells practically indistinguishable from unmodified Trastuzumab. Interestingly, this apparent dissociation constants of this conjugate for the target on tested cell lines was lower by a factor of 5.2-9 times when compared to Trastuzumab conjugated to the same toxin also through stable amide bonds, but using direct (single-step) modification using a non-site selective derivative (NHS ester, data not shown).

Full cytotoxic potential of the antibody-drug conjugates obtained using the methodology presented herein can be exemplified by antibody-drug conjugates of the type C, carrying an example of a mushroom toxin alpha-amanitin with the DAR of approximately 2. This conjugate exhibited a very high cytotoxic activity against several HER-2 positive cancer cell lines, showing values of EC$_{50}$ of 12 pM for SKBR-3 cell line to 0.11 nM for SKOV3 cells (titration curves not shown). A corresponding negative control conjugate of Palivizumab (targeting a viral protein absent in human cells) conjugated to identical toxin with DAR of approximately 2 did not show any toxicity to the same cells at concentrations 3-4 orders of magnitude higher than the active Trastuzumab-based ADC.

The Trastuzumab ADC of type J was prepared and purified in sufficient amounts for animal studies. Its in vivo efficacy was confirmed in two aggressive mouse xenograft models of human mammary gland carcinoma (JIMT-1 model) and gastric carcinoma (NCI-N87 model). Specifically, a full tumor regression was observed in animals injected with 2 mg/kg dose of the ADC (DAR=2) in JIMT-1 model and at 3 mg/kg dose in NCI-N87 model.

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the disclosure described herein. Such equivalents are intended to be encompassed by the following claims.

What is claimed is:
1. A linker-antibody conjugate of Formula IA:

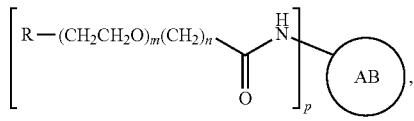

or a pharmaceutically acceptable salt thereof,
wherein
R is a reactive handle selected from the group consisting of alkyne, cycloalkyne, azide, benzyl azide, 1,3-diene, nitrile oxide, nitrone, tetrazine, and a trans-cyclooctene, or their structurally related derivatives capable of undergoing bio-orthogonal cycloaddition to an appropriate corresponding reaction entity;
m is 1-40;
n is 1-20;
p is 1-2; and
AB is an antibody, wherein at least 90% of the linker is site selectively attached to lysine 188 of a kappa light chain constant domain of the antibody based on a Kabat numbering.
2. The linker-antibody conjugate of claim 1, wherein R is azide or benzyl azide.
3. The linker-antibody conjugate of claim 1, wherein R is selected from the group consisting of alkyne, cycloalkyne, azide, benzylazide, 1,3-diene, nitrile oxide, nitrone, tetrazine, and a trans-cyclooctene.
4. The linker-antibody conjugate of claim 1, wherein AB is selected from the group consisting of abciximab, adalimumab, adalimumab-atto, ado-trastuzumab emtansine, alemtuzumab, alirocumab, atezolizumab, avelumab, basiliximab, belimumab, bevacizumab, bezlotoxumab, blinatumomab, brentuximab vedotin, brodalumab, canakinumab, capromab pendetide, certolizumab pegol, cetuximab, daclizumab (Zenapax), daclizumab (Zinbryta), daratumumab, denosumab, dinutuximab, dupilumab, durvalumab, eculizumab, elotuzumab, evolocumab, golimumab, golimumab, ibritumomab tiuxetan, idarucizumab, infliximab, infliximab-abda, infliximab-dyyb, ipilimumab ixekizumab, mepolizumab, natalizumab, necitumumab, nivolumab, obiltoxaximab, obinutuzumab, ocrelizumab, ofatumumab, olaratumab, omalizumab, palivizumab, panitumumab, pembrolizumab, pertuzumab, ramucirumab, ranibizumab, raxibacumab, reslizumab, rituximab, secukinumab, siltuximab, tocilizumab, tocilizumab, trastuzumab, ustekinumab, vedolizumab, sarilumab, rituximab and hyaluronidaseguselkumab, inotuzumab ozogamicin, adalimumab-adbm, gemtuzumab ozogamicin, bevacizumab-awwb, benralizumab, and emicizumab-kxwh. trastuzumab-dkst, infliximab-gbtx, ibalizumab-uiyk, tildrakizumab-asmn, burosumab-twza, and erenumab-aooe.
5. A payload-linker-antibody conjugate of Formula IB:

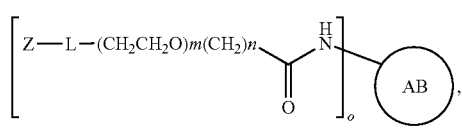

or a pharmaceutically acceptable salt thereof,
wherein
m is 1-40;
n is 1-20;
o is 1-2;

L is a linking moiety selected from —C(O)$C_1$-$C_{30}$-heteroaromatic- or —$C_1$-$C_{30}$-heteroaromatic-C(O)—;

Z is selected from a toxin, a drug, and a chelator payload; and

AB is an antibody, wherein at least 90% of the linker is site selectively attached to lysine 188 of a kappa light chain constant domain of the antibody based on a Kabat numbering.

6. The payload-linker-antibody conjugate of claim 5, wherein L is a linking moiety of the structure:

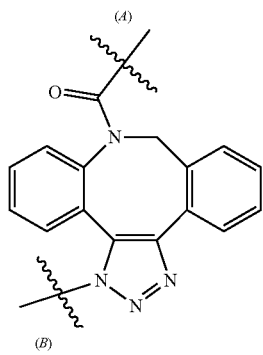

wherein either (A) or (B) are attached to the toxin, drug, or chelator payload.

7. The payload-linker-antibody conjugate of claim 5, wherein AB is selected from the group consisting of abciximab, adalimumab, adalimumab-atto, ado-trastuzumab emtansine, alemtuzumab, alirocumab, atezolizumab, avelumab, basiliximab, belimumab, bevacizumab, bezlotoxumab, blinatumomab, brentuximab vedotin, brodalumab, canakinumab, capromab pendetide, certolizumab pegol, cetuximab, daclizumab (Zenapax), daclizumab (Zinbryta), daratumumab, denosumab, dinutuximab, dupilumab, durvalumab, eculizumab, elotuzumab, evolocumab, golimumab, golimumab, ibritumomab tiuxetan, idarucizumab, infliximab, infliximab-abda, infliximab-dyyb, ipilimumab ixekizumab, mepolizumab, natalizumab, necitumumab, nivolumab, obiltoxaximab, obinutuzumab, ocrelizumab, ofatumumab, olaratumab, omalizumab, palivizumab, panitumumab, pembrolizumab, pertuzumab, ramucirumab, ranibizumab, raxibacumab, reslizumab, rituximab, secukinumab, siltuximab, tocilizumab, tocilizumab, trastuzumab, ustekinumab, vedolizumab, sarilumab, rituximab and hyaluronidaseguselkumab, inotuzumab ozogamicin, adalimumab-adbm, gemtuzumab ozogamicin, bevacizumab-awwb, benralizumab, and emicizumab-kxwh. trastuzumab-dkst, infliximab-qbtx, ibalizumab-uiyk, tildrakizumab-asmn, burosumab-twza, and erenumab-aooe.

8. The payload-linker-antibody conjugate of claim 6, wherein (A) or (B) is a chelator.

9. The payload-linker-antibody conjugate of claim 8 wherein the chelator is macropa.

10. The payload-linker-antibody conjugate of claim 6, wherein (A) or (B) is a toxin.

11. The payload-linker-antibody conjugate of claim 10, wherein the toxin is alpha amanitin.

* * * * *